(12) United States Patent
Gellman et al.

(10) Patent No.: US 8,021,570 B2
(45) Date of Patent: Sep. 20, 2011

(54) β-PEPTIDE LYOTROPIC LIQUID CRYSTALS AND METHODS OF MANUFACTURE AND USE THEREOF

(75) Inventors: Samuel H. Gellman, Madison, WI (US); Nicholas L. Abbott, Madison, WI (US); William C. Pomerantz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1133 days.

(21) Appl. No.: 11/762,574

(22) Filed: Jun. 13, 2007

(65) Prior Publication Data
US 2010/0021344 A1   Jan. 28, 2010

Related U.S. Application Data

(60) Provisional application No. 60/813,201, filed on Jun. 13, 2006.

(51) Int. Cl.
C09K 19/06 (2006.01)
C09K 19/54 (2006.01)
B01J 19/00 (2006.01)
G01N 33/68 (2006.01)
C07K 1/02 (2006.01)

(52) U.S. Cl. ............. 252/299.01; 252/299.5; 252/299.6; 422/68.1; 436/86; 436/90; 977/705; 530/333; 530/338

(58) Field of Classification Search ............. 252/299.01, 252/299.5, 299.6; 349/199; 424/68.1; 436/86, 436/90; 530/300, 330, 333, 338; 977/705; 422/68.1
See application file for complete search history.

(56) References Cited

U.S. PATENT DOCUMENTS

| 6,284,197 | B1 | 9/2001 | Abbott et al. |
| 2002/0041854 | A1 | 4/2002 | Hadasch et al. |

FOREIGN PATENT DOCUMENTS

| WO | 9209695 A | 6/1992 |
| WO | 9306921 A | 4/1993 |
| WO | 2005038430 A | 4/2005 |
| WO | 2006002141 A | 1/2006 |
| WO | 2006063174 A | 6/2006 |

OTHER PUBLICATIONS

Weise et al., "Conformational Analysis of Alanine Dipeptide from Dipolar Couplings in a Water-Based Liquid Crystal", J. Phys. Chem. B 2003, 107, 3265-3277.*
CAPLUS 1995: 115361.*
International Search Report of PCT/US2007/071120.

* cited by examiner

*Primary Examiner* — Shean Wu
(74) *Attorney, Agent, or Firm* — Joseph T. Leone, Esq.; DeWitt Ross & Stevens S.C.

(57) ABSTRACT

The present invention provides materials and methods that make liquid crystal phases accessible with relatively short β-peptides in aqueous solvents.

20 Claims, 21 Drawing Sheets

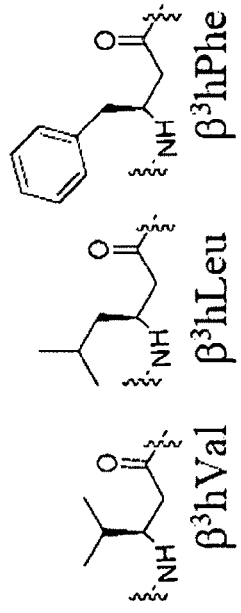

Hydrophobic scan of β³hTyr-(ACHC-ACHC-β³hLys)₃

(ACHC-ACHC-β³hLys)₃ 10 wt%  β³hTyr-(ACHC-ACHC-β³hPhe-β³hLys)₃ 10 wt%  β³hTyr-(ACHC-ACHC-β³hVal-β³hLys)₃ 10 wt%  β³hTyr-(ACHC-ACHC-β³hLeu-β³hLys)₃ 10 wt%

- LLC phase formation sensitive to changes at N-terminus
- LLC phase formation sensitive to changes along hydrophobic face
- ACHC important for assembly not just for structure β³hPhe
β³hLeu
β³hVal

Fig. 6

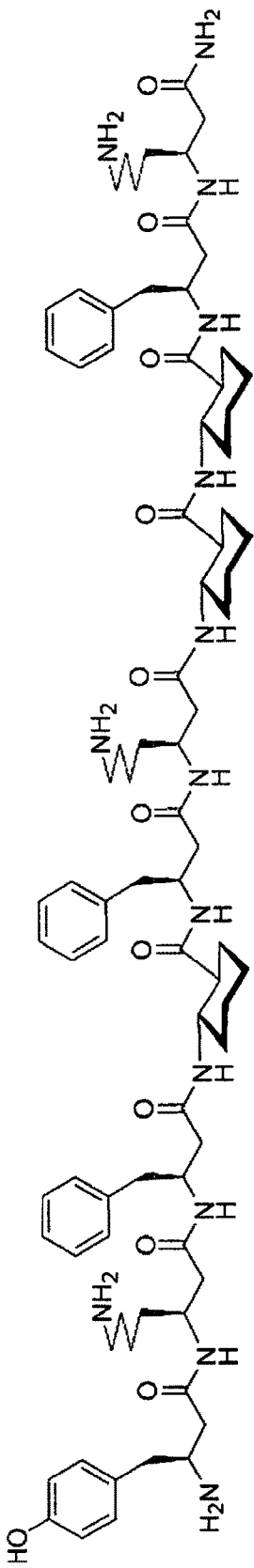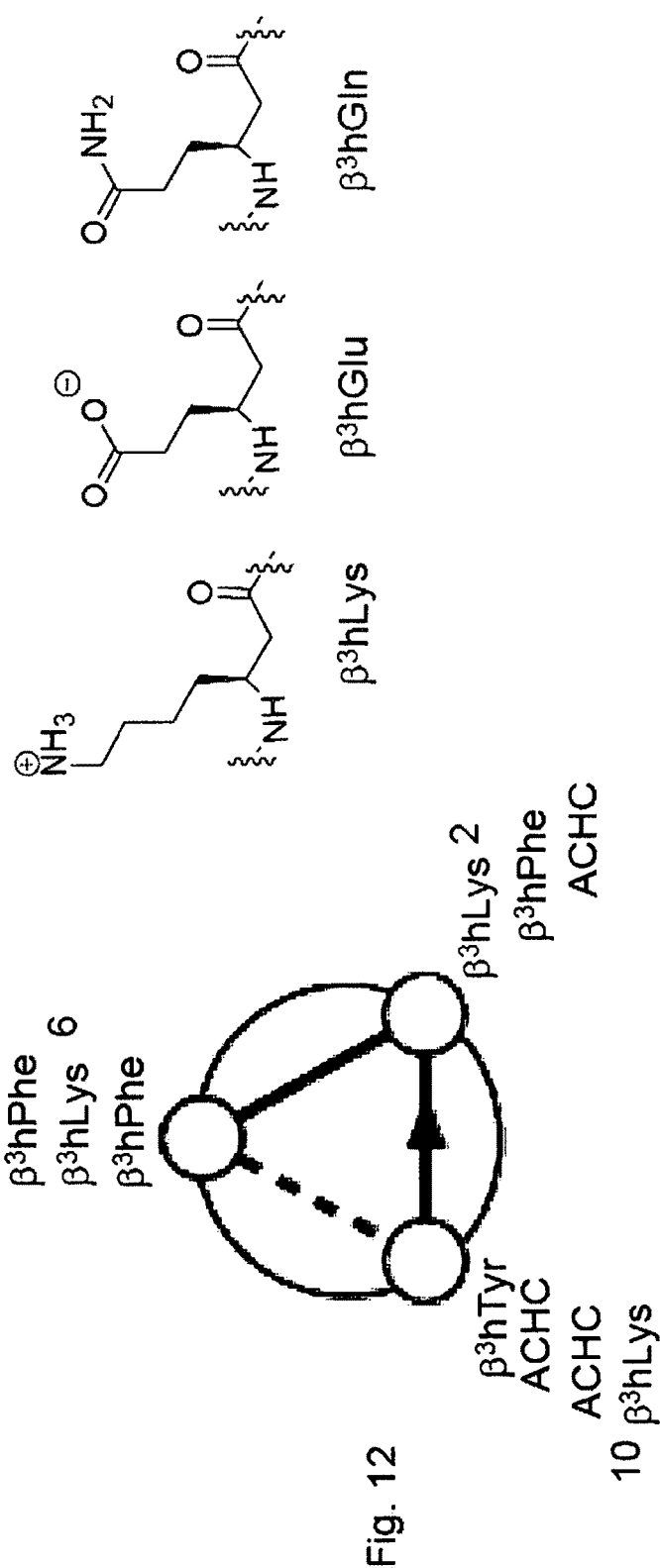
Fig. 12

+ (pH 6.5)      - (SDeS)
DSCG 16%      5-Y-(ACHC2K)3 1 wt%
Fig. 22

Aggregate Morphology Analysis (Cryo-TEM)
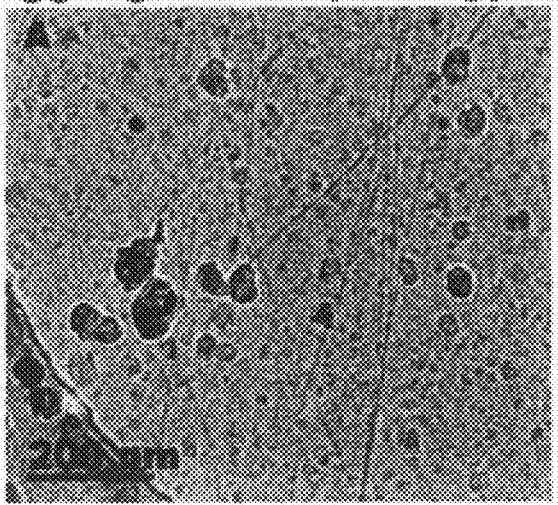
2% Fibers/small aggregates
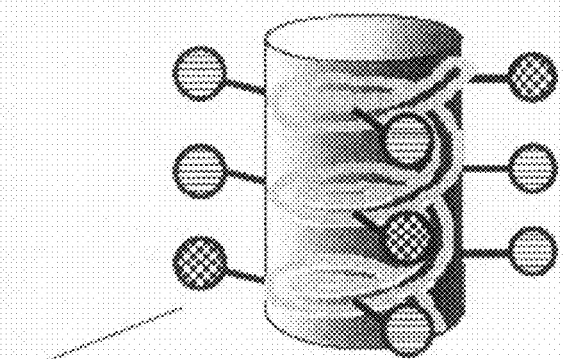
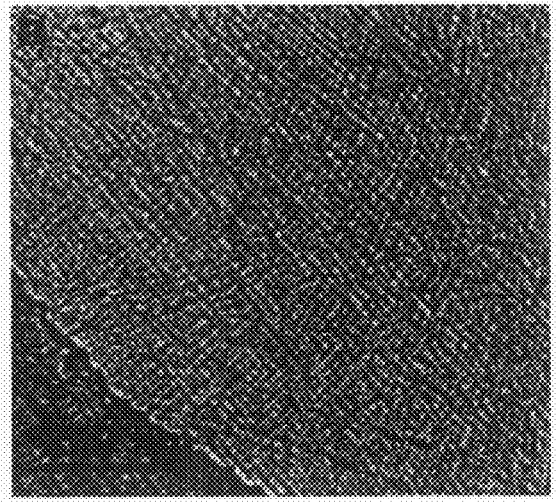
8%, dense network of fibers
Fig. 23

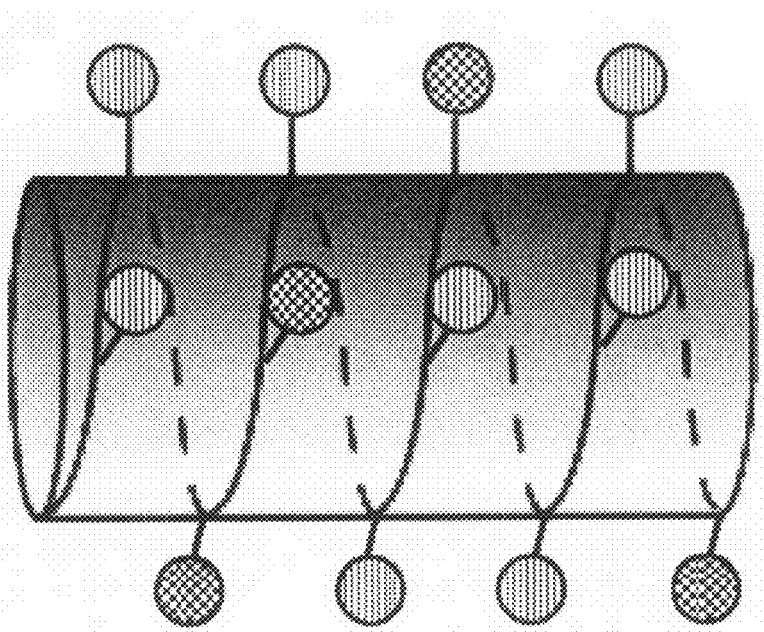
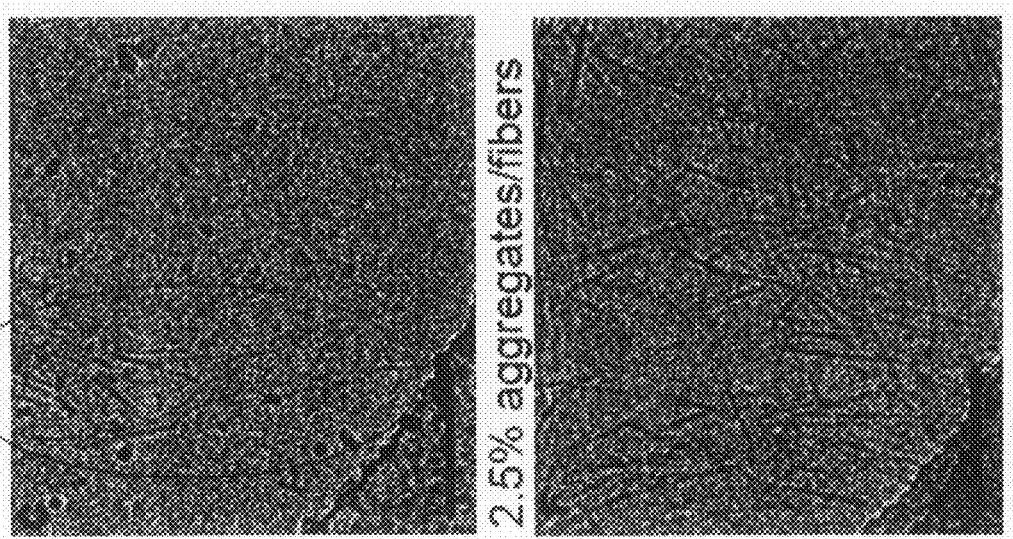
Fig. 25

β-PEPTIDE LYOTROPIC LIQUID CRYSTALS AND METHODS OF MANUFACTURE AND USE THEREOF

CROSS REFERENCE TO RELATED APPLICATION

The present application claims the benefit of U.S. Provisional application 60/813,201, filed Jun. 13, 2006, which is incorporated herein by reference in its entirety for all purposes.

STATEMENT REGARDING FEDERALLY SPONSORED RESEARCH AND DEVELOPMENT

This work was supported in part by awards from the United States government—grant DMR-0425880 from the National Science Foundation. The Government of the United States may have certain rights in this invention.

FIELD OF THE INVENTION

This invention is generally directed to liquid crystal technology. In particular, this invention is directed to the design, manufacture and use of β-peptide-based liquid crystals.

BACKGROUND OF THE INVENTION

Liquid crystals (LCs) are extensively used for applications that include display and sensing technologies. Design of new lyotropic liquid crystals (liquid crystalline phases that form in the presence of solvent) has been limited relative to the design of LCs that form without solvent. Lyotropic liquid crystals have been recently used in directing polymerization reactions, protein structure determination, templating inorganic materials, aligning carbon nanotubes and bio-sensing. Because of this functional diversity, identification of new molecules capable of forming lyotropic LC phases (mesogens) remains an important goal.

Lyotropic liquid crystalline phases that form in water have been created with surfactants, aromatic dyes, synthetic polymers and biopolymer assemblies such as DNA, viruses, polysaccharides, collagen, and other polypeptides. Systematic evaluation of factors that modulate LC behavior is often difficult in these systems because rational and incremental modification of mesogen structure is not readily achieved.

It is well-known that α-helical poly(α-amino acids) are capable of forming lyotropic liquid crystalline phases. Poly-α-peptides must be quite long, however, to form LC phases. In general, this length requirement has necessitated the use of materials that are polydisperse in size and limited in sequence, which has hampered exploration of sequence-property correlations. Short oligomers of beta-amino acids (beta-peptides) are attractive for systematic study of assembly processes because beta-peptides can display a diverse range of functionalized side chains, and these oligomers fold into compact and stable conformations that orient the side chains in predictable ways. Beta-peptides have been shown to self-assemble in dilute solution and on gold surfaces, as well as to associate with microbial membranes.

Accordingly, it is desirable to design and synthesize modular scaffolds based on beta-peptides for use in LC phase behavior studies and, ultimately, industrial applications.

SUMMARY OF THE INVENTION

The present invention provides materials and methods that make LC phases accessible with relatively short helical beta-peptides ("β-peptides"). Such foldamers display higher helix stability, on a per-residue basis, than do α-peptides when cyclically constrained beta-amino acids ("β-amino acids") such as trans-2-aminocyclohexanecarboxylic acid (ACHC) are used. If short β-peptide oligomers form LC phases in water, then the perfect control of sequence, composition, and length made possible by solid-phase synthesis can be used to probe relationships between β-peptide structure and liquid crystallinity. Knowledge of these relationships then provides guidance for mesogen designs directed toward specific industrial applications including, but not limited to, bio-sensing and chemical reaction templating.

The present invention is directed to a new type of mesogen, namely, oligomers containing β-amino acids ("P-peptides") and the capacity of these materials to form lyotropic liquid crystalline phases in aqueous environments. All reference to amino acids or peptides herein shall be to β-amino acids or β-peptides unless expressly-indicated otherwise.

The term "lyotropic liquid crystal," as used herein, refers to a liquid crystalline material in which ordering effects are induced by changing the respective material's concentration within a solvent. Lyotropic liquid crystals according to the present invention comprise β-peptide containing liquid crystalline materials in aqueous solvents.

Accordingly, a first aspect of the present invention is directed to a lyotropic liquid crystal comprising a β-peptide. In certain embodiments, the β-peptide is globally amphiphilic. As used herein, the term "globally amphiphilic" shall mean that in the helical conformation of a beta-peptide, there is a surface dominated by lipophilic side chains running along one side of the helix, and a second surface dominated by hydrophilic side chains running along the opposing side of the respective helix. Global amphiphilicity may be recognized when a beta-peptide is rendered as a helix wheel diagram (i.e., a graphical convention that displays the helical beta-peptide conformation along the helix axis). In preferred embodiments, the β-peptide has the structure: R-(ACHC-ACHC-$\beta^3$-hLys)$_n$, wherein n is 2-4 and R is $\beta^3$-hTyr or $\beta^3$-h-para-Cl-Phe. In particularly preferred embodiments, the β-peptide is $\beta^3$-hTyr-(ACHC-ACHC-$\beta^3$-hLys)$_2$ or $\beta^3$-hTyr-(ACHC-ACHC-$\beta^3$-hLys)$_3$. Alternatively, the β-peptide has the structure R-(ACHC-ACHC-$\beta^3$-hLys)$_3$ wherein R is $\beta^3$-hTyr or $\beta^3$-h-para-Cl-Phe and $\beta^3$-hLys at position 10 is substituted by $\beta^3$-hGlu.

In other embodiments, the lyotropic liquid crystal according to the invention includes a β-peptide that is globally non-amphiphilic. The term "globally non-amphiphilic" shall refer to beta-peptides that substantially-lack the two opposing lipophilic and hydrophilic surfaces of globally amphiphilic beta-peptides but, nonetheless, form liquid crystals useful in the present invention based on selection of appropriate mesogenic groups and helical size, as described herein. Preferred embodiments of such β-peptides include the entities shown in FIG. 10 including, for example, $\beta^3$-hTyr-(ACHC-$\beta^3$-hPhe-$\beta^3$-hLys)$_3$ scram, $\beta^3$-hTyr-(ACHC-$\beta^3$-hPhe-$\beta^3$-hLys)$_4$ scram1, or $\beta^3$-hTyr-(ACHC-$\beta^3$-hPhe-$\beta^3$-hLys)$_4$ scram2.

In yet other embodiments, a lyotropic liquid crystal according to the invention includes a β-peptide having the structure CH$_3$(CH$_2$)$_n$CONH-$\beta^3$-hTyr-(ACHC-ACHC-$\beta^3$-hLys)$_3$ wherein n is 0-5. Certain other beta-peptides according to the invention are functionalized with a biological moiety such as, for example, biotin, as in the β-peptide having the structure: biotin-$\beta^3$-hGly-$\beta^3$-hTyr-(ACHC-ACHC-$\beta^3$-hLys)$_3$.

In another aspect, the invention is directed to a method of providing a β-peptide-based lyotropic liquid crystal. Such a method includes the step of combining β-peptides capable of self-assembly under conditions to allow the self-assembly to occur whereby a lyotropic liquid crystal is provided. Methods according to the invention utilize β-peptides as described and claimed herein.

In yet another aspect, the invention encompasses a liquid crystal device for detecting an analyte in a sample. Such a device includes: (a) a sample chamber; and (b) a β-peptide-based lyotropic liquid crystal positioned within the sample chamber. Devices according to the invention utilize β-peptides as described and claimed herein.

The invention also includes methods of identifying a β-peptide capable of forming a lyotropic liquid crystal in an aqueous solvent. Such methods includes steps of: (a) obtaining a candidate β-peptide; (b) placing the candidate β-peptide in an aqueous solvent under conditions to promote formation of a lyotropic liquid crystal; and (c) detecting the formation of the lyotropic liquid crystal wherein such formation identifies the candidate β-peptide as capable of forming a lyotropic liquid crystal in an aqueous solvent. In preferred methods, the detecting step (c) is carried out using polarized light wherein optical birefringence of the candidate β-peptide indicates formation of the lyotropic liquid crystal. In other embodiments, the method is carried out in parallel on multiple candidate β-peptides.

Yet another aspect of the invention is directed to a method of providing a network of self-assembled nanofibers. Such a method includes the step of combining β-peptides capable of self-assembly under conditions to allow the self-assembly to occur whereby a network of self-assembled nanofibers is provided. It is preferred that at least one of the β-peptides capable of self-assembly is a β-peptide as described and claimed herein.

These and other features and advantages of various exemplary embodiments of the methods according to this invention are described, or are apparent from, the following detailed description of various exemplary embodiments of the methods according to this invention.

BRIEF DESCRIPTION OF THE FIGURES

Various exemplary embodiments of the methods of this invention will be described in detail, with reference to the following figures, wherein:

FIG. 6 provides optical micrographs of aqueous solutions of beta-peptides derived from 3 between crossed polarizing filters. From left panel to right panel, a hydrophobic scan of 3 indicates that the deletion of the N terminal β$^3$-hTyr group, or the substitution of β$^3$-hVal, β$^3$-hLeu or β$^3$-hPhe for half the ACHC residues in 3 results in an analog beta-peptide unable to form a liquid crystal phase.

FIG. 12 illustrates various analog beta-peptides based on β$^3$-hTyr-(ACHC-β$^3$-hPhe-β$^3$-hLys)$_3$. Hydrophilic substitutions included β$^3$-hGlu and β$^3$-hGln residues at the β$^3$-hLys position 2, 6 or 10.

FIG. 22 provides fluorescent images of fluorescently labeled biotin bound to gold slides displaying streptavidin after prior incubation with top left) pH 6.5 aqueous solution, Top right) 32 wt % solution of sodium decyl sulfate (known to denature proteins) Bottom right) 16 wt % sample of DSCG, a known lyotropic liquid crystal Bottom left) 1 wt % of LC forming β-peptide pentanoyl-NH-β$^3$hTyr-(ACHC-ACHC-β$^3$hLys)$_3$.

FIG. 23 provides cryo-TEM micrographs of A and top) A, 2 wt %, bottom) A, 8 wt %.

FIG. 25 depicts cryo-TEM micrographs of -β³hTyr -(ACHC-β³hPhe-β³hlys) 4-scram1 A) 2.5 wt %, B) 5 wt %.

DETAILED DESCRIPTION OF THE INVENTION

Figure 1:
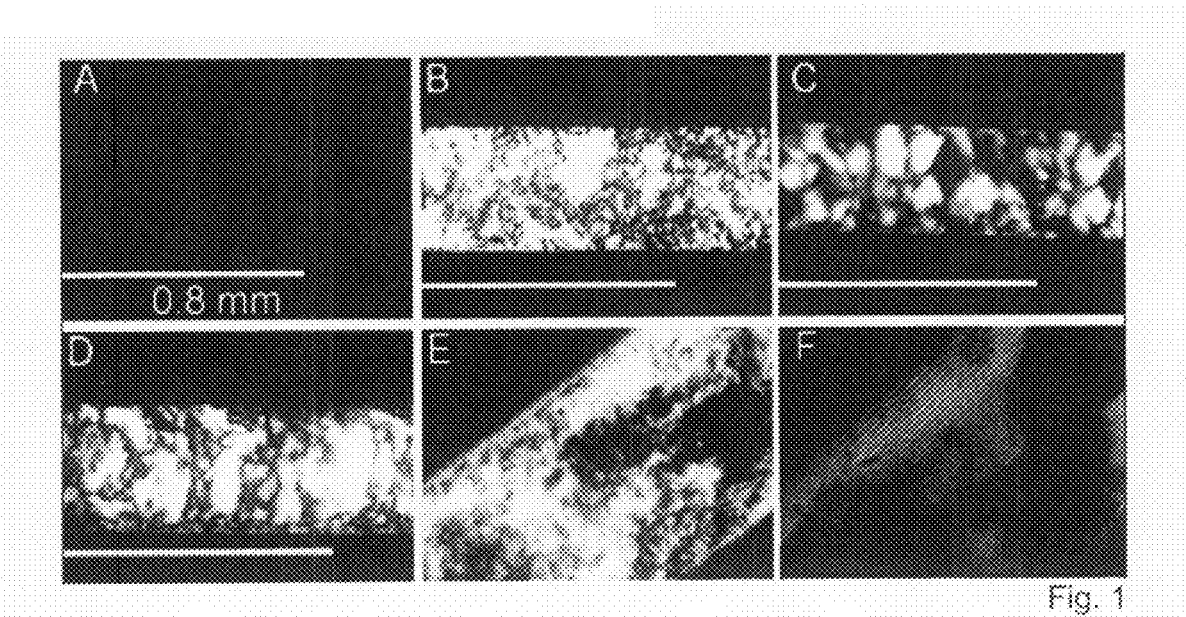
FIG. 1 illustrates optical micrographs of aqueous solutions of β-peptides 1-3 between crossed polarizing filters. A) 1, 25 wt %. B) 2, 19 wt %. C) 3, 10 wt %. D) Ac-3, 2.5 wt %. E) 2×2, 19 wt %. F) 2.5×3, 10 wt %.

The present invention provides lyotropic liquid crystal-forming molecules based on a β-peptide scaffold. β-Peptides differ from conventional peptides in that certain β-peptides are capable of forming stable-helices at short oligomeric lengths, giving rise to robust asymmetric structures. The modular synthesis of β-peptides allows for spatial control over the display of functionalized side chains, including ionic groups, which confer aqueous solubility, and aromatic groups, which influence liquid crystal properties.

In certain embodiments, the invention provides liquid crystals manufactured from globally amphiphilic β-peptide helices; helices that display lipophilic groups on one side and hydrophilic groups on the other side. In other embodiments, global amphilicity is not a necessity so long as appropriate mesogenic groups and helical size are selected, as described herein. It can be appreciated that the present invention offers sequence flexibility so that LC mesogens may be tailored in respect to, among many properties, viscosity or birefringence. Lyotropic LCs according to the present invention are formed in aqueous environments (i.e., water-based) and, because of their β-peptide content, are highly resistant to proteolytic degradation. Accordingly, LCs according to the invention are useful in a wide variety of applications, including but not limited to, qualitative and/or quantitative biolo-molecular sensing of proteins, cells, or viruses (generally, "analytes") in biological samples.

Oligomers of beta-amino acids may incorporate chemical groups and/or small molecules that, in general, further functionalize the resulting liquid crystal. In preferred embodiments, the present invention encompasses certain oligomers of beta-amino acids that incorporate aromatic groups to maximize the optical birefringence of corresponding liquid crystals. Oligomers may also incorporate polymers of, for example, ethylene glycol to enhance biocompatibility of the liquid crystal. The artisan can appreciate that the use of beta-peptides also permits introduction of other chemical functional groups, including, but not limited to, light sensitive groups such as azobenzene and/or redox-active groups such as ferrocene. In another preferred embodiment, chemical groups or small molecules (e.g. biotin or a carbohydrate) may be provided that bind to biological and/or detecting surfaces/targets. Such a functionalized oligomer having a biotin group attached is described in the Examples section. Oligomers of beta-amino acids may, for example, include thiol groups that interact with the surfaces of gold films. The beta-peptides may, in other embodiments, include chemical functional groups such as aromatic ring structures and stacked aromatic ring structures that enhance the electrical conductivity of the organized assemblies formed by beta-peptides.

Liquid crystals formed according to the invention are not limited in their composition to only amino acids of the beta variety. Certain liquid crystals of the invention may, for example, include combinations of both beta- and alpha-amino acids. The incorporation of alpha-amino acids in the oligomer is advantageous in providing, for example, biological functionality such as ligand recognition. A non-limiting example of such is the tripeptide RGD, which recognizes integrins, and may be incorporated into mixed oligomers used to form liquid crystals for biosensing applications.

As can be appreciated, oligomers according to the present invention are useful in a broad range of applications beyond LC bio-sensing. Nanofibers composed of self-assembling peptides are a class of material which have found use in, for example, cell culture, tissue engineering, cell therapy, protein recruitment, biomineralization, organizing and templating synthesis of inorganic/organic "nanowires", and electrical conduction and insulation. The following is a non-exhaustive citation list illustrating the diverse set of applications in which nanofibers find use: Davies, et al. *Proc. Natl. Acad. Sci,* 2006, 103, 8155-8160 (application of biotinylated peptide nanofibers to improve cell therapy for myocardial infarction); Guler, et al. *Nano Lett.* 2005, 5, 249-252 (peptide nanofibers which display RGD sequences and biotin for protein and cell recognition to enable cell adhesion); Ryadnov, et al., *Am. Chem. Soc.* 2004, 126, 7454-7455 (using self-assembling peptide fibers to recruit proteins displaying gold nanoparticles by displaying biotin or antibody FLAG tags); Ellis-Behnke, et al. *Proc. Natl. Acad. Sci* 2006, 103 5054-5059 (self assembling peptide fibers used as a potential therapeutic for brain damaged tissue, and axon regeneration); Reches, et al. *Science,* 2003 625-627 (hollow nanofibers used to template the growth of silver nanowires); Yemini, et al. *Nano Lett.* 2005, 5, 183-186 (nanotubes composed of aromatic residues shown to be a conductive material and used as an electrochemical sensor for hydrogen peroxide); Scheibel, et al. *Proc. Natl. Acad. Sci.* 2003, 100, 4527-4532 (peptide nanofibers covalently linked to gold nanoparticles shown to form a conductive material with high temperature and pH stability); Hartgerink, et al. *Science* 2001, 294, 1684-1688 (self-assembling peptide fibers shown to promote biomineralization); and Jun, et al. *Adv. Mater.* 2005, 1 7, 2612-2617 (using networks of self-assembling peptide fibers to mimic the endothelial cellular matrix for tissue engineering).

Reviews directed to nanofiber technology include: Woolfson, et al. "Peptide-based fibrous biomaterials: some things old, new, and borrowed, in *Curr. Opin. Chem. Biol.,* 2006, 11, 559-567; Jun, et al.; "Biomimetic self-assembled nanofibers" in *Soft Matter,* 2006, 2, 177-181; and Zhoa, et al., Designer Self-Assembling Peptide Materials, in *Macromol. Biosci.,* 2007, 7, 13-22; and Chem Rev 2005, 105, 1401-1143 (all citations in the this and the preceding paragraph are incorporated herein by reference).

In yet another aspect, the invention encompasses a liquid crystal device for detecting an analyte in a sample. Such a device includes: (a) a sample chamber; and (b) a β-peptide-based lyotropic liquid crystal positioned within the sample chamber. Devices according to the invention utilize β-peptides as described and claimed herein. Liquid crystal devices adaptable to use with β-peptide-containing liquid crystals according to the invention include, but are not limited to, those previously-described by Abbott et al. (e.g., see U.S. Published Patent applications 2002/0028451 A1, 2002/0164604 A1, 2003/0194753 A1, 2004/0038408 A1, 2005/0064395 A1, 2005/0079487 A1, and 2006/003389 A1, all of which are incorporated by reference herein).

In part, the present invention is related to the inventors' determination that β-peptides can self-assemble to form lyotropic liquid crystalline (LC) phases in water. To illustrate the invention, β-peptides 1-4, depicted in the examples section below, were designed to form 14-helices of increasing length. Optical microscopy showed that several of these β-peptides formed LC phases in aqueous solutions at concentrations as low as 2.5 wt % (15 mM). Thermal stability and reversibility of LC phase formation for β-peptide 3 was assessed by variable temperature $^2$H NMR spectroscopy and optical microscopy. The LC phase formed by β-peptide 3 at 10 wt % was disrupted above 40° C. in $D_2O$ and, advantageously, reformed within minutes upon cooling. The data disclosed herein demonstrate that highly folded 14-helical β-peptides can produce LC phases at shorter lengths than do α-helical α-peptide mesogens and provide a basis for tailoring properties of LC phases for applications including, but not limited to, biomolecular sensing. Further advantages of LCs formed according to the invention include, but are not limited to: (a) typically low weight % lyotropic LC formation in aqueous environment as compared to prior materials; (b) viscosity of beta-peptide solutions tunable as compared to a majority of prior materials; and (c) generally high birefringence of lyotropic LCs fabricated with beta-peptides (i.e., ease of detection).

The example section below provides the artisan with a detailed description of the preferred method of producing β-peptide components by microwave-assisted solid phase synthesis. It is certainly envisioned that the production of β-peptide components may be carried out by parallel or split-and-mix syntheses to provide libraries of β-peptides that, if desired, may be screened by combinatorial methods for identification of potentially-novel β-peptides useful in lyotropic LC manufacture. Syntheses for the production of β-peptide libraries that are adaptable to the present invention include, but are not limited to, those described by Murray et al. (*J. Am. Chem. Soc.* (2005) 127:13271-13280; *J. Comb. Chem.* (2006) 8:58-65). For example, β-peptides may be synthesized on beads and then released in small volumes for screening by polarized light to detect candidate molecules exhibiting optical birefringence. In certain screening strategies, such screening may be carried out in micro- or nano-fluidic channels.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Globally Amphiphilic Beta-peptide Lyotropic Liquid Crystals

The inventors prepared homologous series 1-4, shown below, to evaluate their design strategy. Peptide 5 is a sequence isomer of 3. 14-Helical β-peptide sequences 1-5 are shown as are helical wheel diagrams of 3 and 5. The abbreviation "ACHC" indicates trans-2-aminocyclohexane carboxylic acid. The "+" symbol denotes $β^3$-hLys.

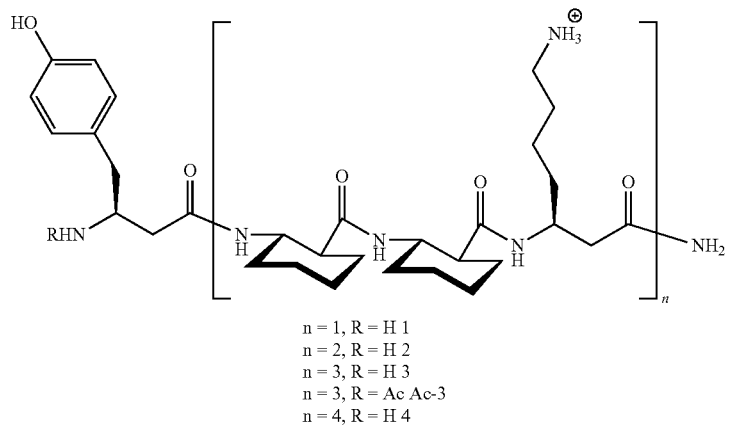

n = 1, R = H 1
n = 2, R = H 2
n = 3, R = H 3
n = 3, R = Ac Ac-3
n = 4, R = H 4

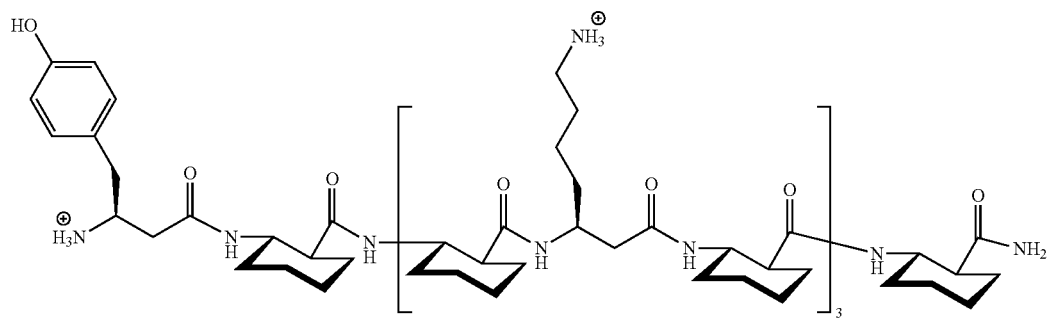

5

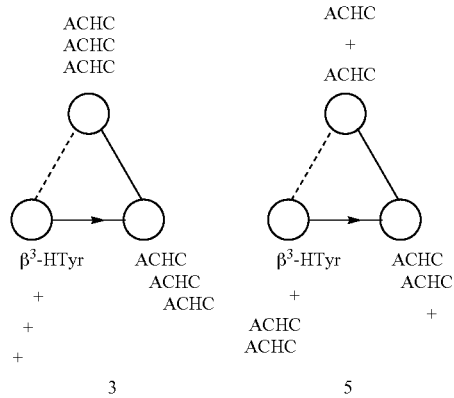

Extensive structural analysis of closely related beta-peptides allowed the inventors to determine that 1-4 will adopt the 14-helical conformation, a secondary structure that is defined by 14-membered ring C=O(i)—H—N(i-2) H-bonds between backbone amide groups and that has approximately three β-amino acid residues per turn of helix. In 1-4 the number of ACHC-ACHC-β³-hLys triads increases from one to four. This sequence design generated folded conformations displaying a global segregation of hydrophobic ACHC residues on one face of the 14-helix and hydrophilic β³-hLys residues on the other face (lower left wheel diagram, above). This global amphiphilicity was intended to promote hydrophobically driven self-assembly in aqueous solution. β-Peptide 5, a sequence isomer of 3, did not allow global segregation of ACHC and β³-hLys residues in the 14-helical state (lower right wheel diagram, above). Previous studies in dilute solution had shown that the enantiomer of 3 self-associated into small soluble aggregates while the non-globally amphiphilic isomer, ent-5, remained monomeric.

Figure 3:
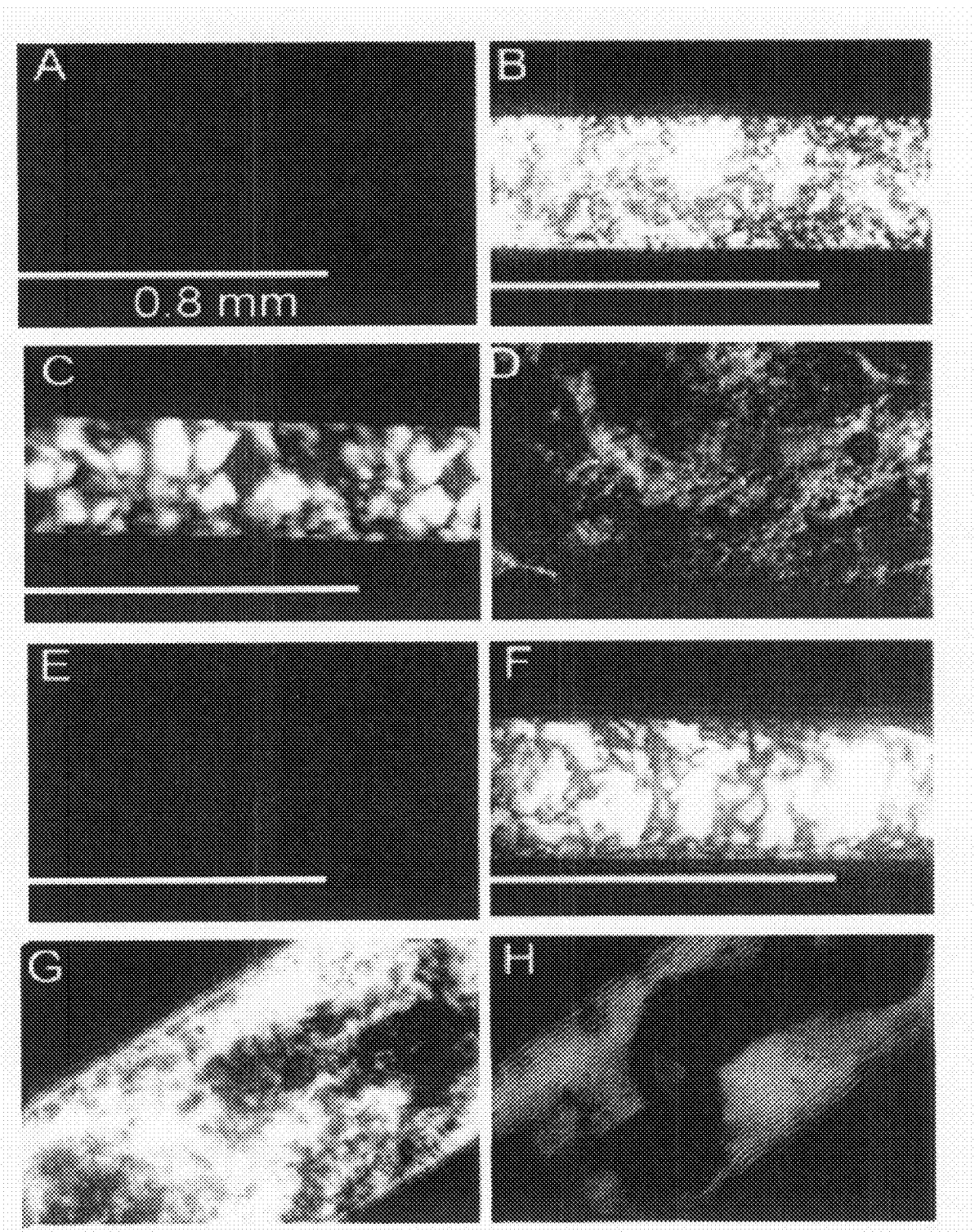
FIG. 3 shows optical micrographs of aqueous solutions of beta-peptides 1-5 between crossed polarizing filters. A) 1, 25 wt %. B) 2, 19 wt %. C) 3, 10 wt %. D) 4 gel, 2 wt %. E) 5, 15 wt %. F) Ac-3, 2.5 wt %. G) 20×2, 19 wt %. H) 20×3 10 wt %.

The inventors used optical microscopy for initial evaluation of aqueous solutions of 1-5. For each β-peptide, aqueous solutions of varying concentration were drawn into microcapillaries and examined between crossed polarizing filters at room temperature (FIGS. 1 and 3). In such experiments, the observation of birefringence is taken as evidence of LC phase formation. No birefringence was observed for the shortest β-peptide, tetramer 1, up to 25 wt % (410 mM, FIG. 1A), but heptamer 2 displayed birefringence at 19 wt % (180 mM, FIG. 1B). The marbled optical texture (FIG. 1E) suggested that 2 forms a nematic LC phase under these conditions. Increasing β-peptide length by one triad, to generate 3, led to LC behavior at lower concentrations, as shown by the image obtained for a 10 wt % sample (61 mM, FIG. 1C). In this case, the "fingerprint" pattern evident upon closer inspection (FIG. 1F) suggests a cholesteric LC phase. Thus, self-assembly of the chiral helix formed by 3 induced a helical ordering of molecules in the LC phase whereas the two-turn, chiral helix formed by 2 was unable to induce this higher ordered phase. While no one theory of operation is adopted herein, this behavior may be rationalized by proposing that 3 displays a greater expanse of hydrophobic surface than does 2, leading to stronger intermolecular attraction for 3 than for 2. Further lengthening seems to cause even more avid self-assembly, as aqueous solutions of 2 wt % 4 phase-separate into an isotropic liquid (i.e., non-liquid crystalline) and a gel, which is birefringent. The behavior of 5, the sequence isomer of 3 that cannot form a globally amphiphilic 14-helix, supports a design strategy that hydrophobically driven interactions among β-peptides are crucial for LC phase formation, because 5 displays no birefringence at the highest concentration tested, 15 wt %. Even upon slow evaporation of the concentrated sample of 5, birefringence was not observed (as shown in FIG. 3).

Figure 4:
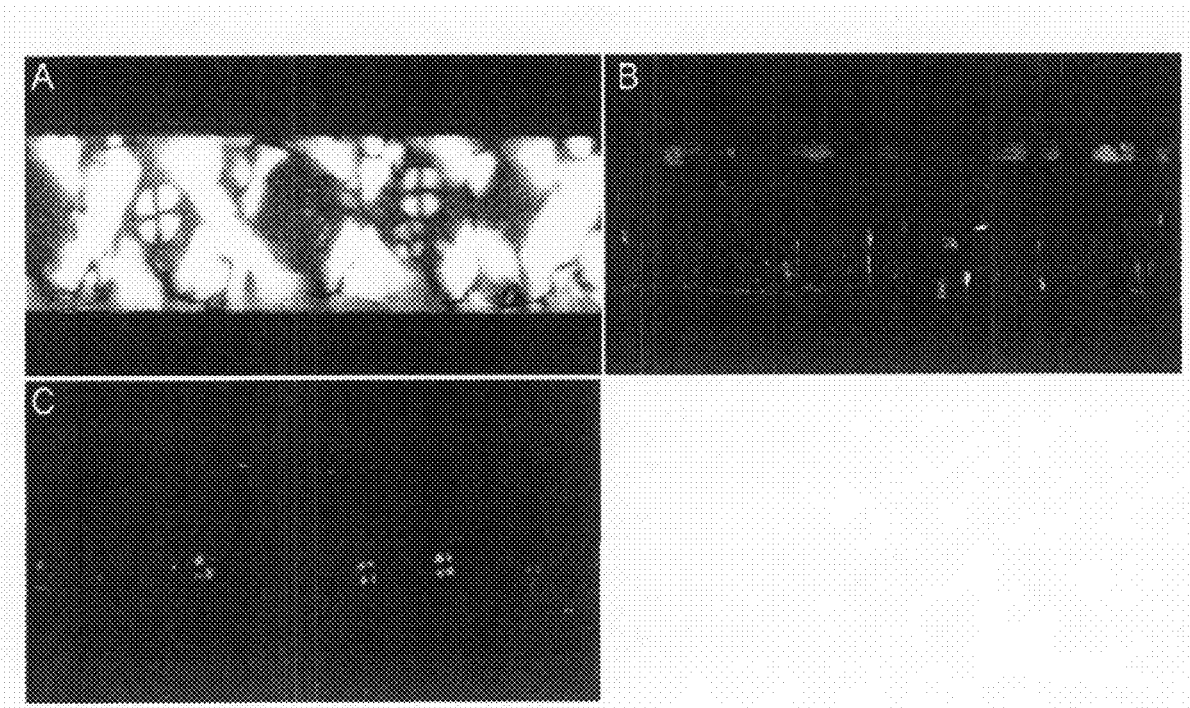
FIG. 4 provides optical micrographs of varying concentrations of 3 between crossed polarizing filters. A) 9.3 wt %. B) 8.4 wt %. C) 7.7 wt %. Nematic droplets in A-C indicate a co-existence state of both the LC and isotropic phase.

The inventors next determined the behavior of 3 in greater detail by varying concentration as well as net charge. Dilution of a 10 wt % sample of 3 to 8 wt % induced a co-existence state in which both the isotropic and LC phases were observable, as shown in FIG. 4. This co-existence state was indicated by the presence of nematic droplets. Dilution to 7 wt % completely abolished the LC phase. Acetylation of the N-terminus to generate Ac-3 reduced the concentration of -peptide necessary for LC phase formation to 2.5 wt % (15 mM, FIG. 1D). This result implies that diminution of electrostatic repulsion can have a profound effect on LC formation. Similar trends have been observed among β-strand-forming alpha-peptides that display LC behavior.

Figure 2:
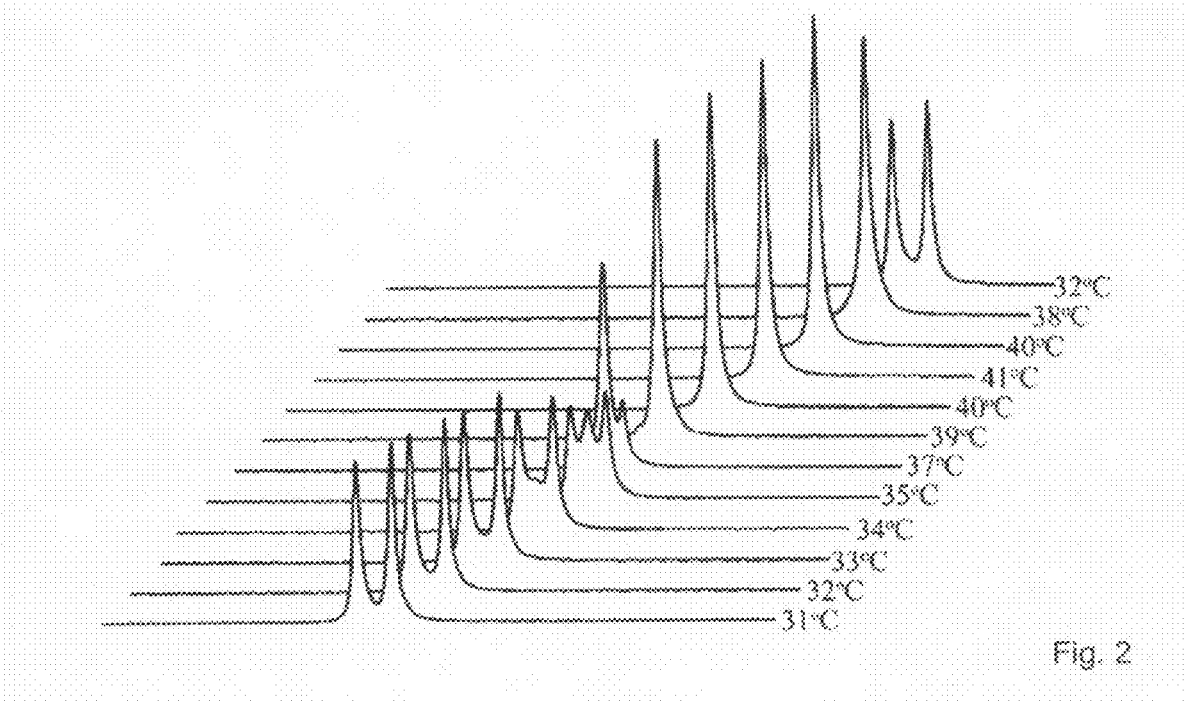
FIG. 2 depicts $^2$H NMR spectra of a 10 wt % solution of 3 in $D_2O$ at various temperatures (10 minute equilibration before data acquired).
Figure 5:
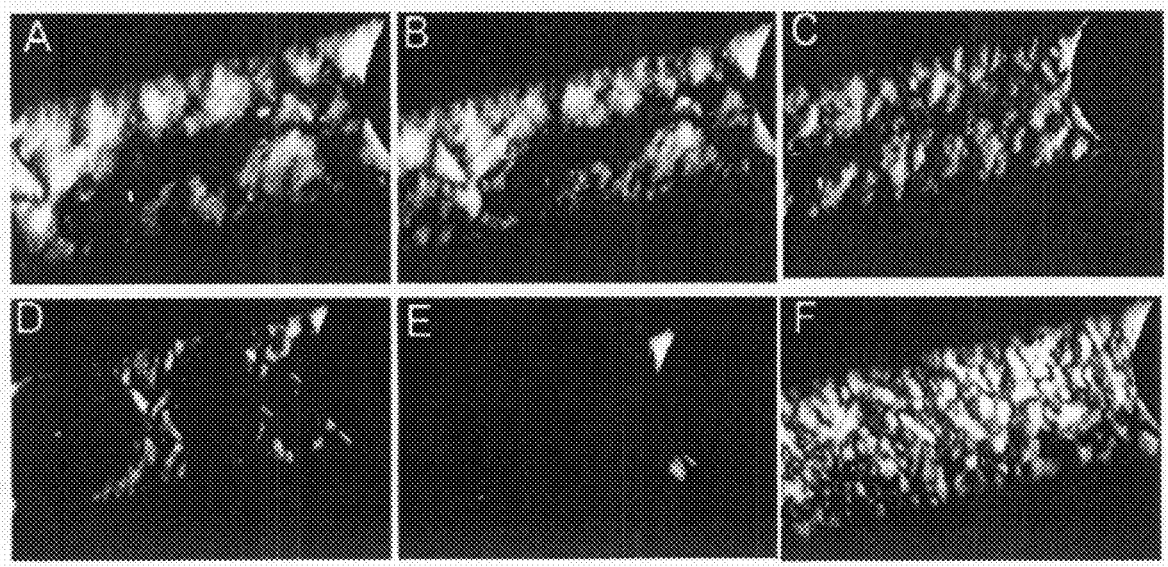
FIG. 5 depicts optical micrographs of 3 at 10 wt % in $D_2O$ between crossed polarizing filters at various temperatures. A) 24° C. B) 28° C. C) 32° C. D) 40° C. E) 50° C. F) rapid cooling to 15° C.

The inventors then made NMR measurements to further characterize the LC phase formed by 3. If a liquid crystalline phase is formed in $D_2O$, the quadrupolar coupling between the D atoms gives rise to characteristic D-NMR line shapes. FIG. 2 shows the effect of temperature on LC phase formation by β-peptide 3 (10 wt %) in $D_2O$. At or below 31° C. the $D_2O$ resonance is split, indicating the existence of an LC phase. As the temperature is raised, a third resonance grows in between the two branches of the doublet; this third resonance arising from $D_2O$ in an isotropic environment. Around 40° C. only the isotropic resonance is observed, but upon cooling the LC doublet reappears, which indicates that LC formation is reversible on a timescale of minutes. These observations are consistent with optical microscopy of a 10 wt % sample of 3 at varying temperatures, as shown in FIG. 5. The NMR approach is superior to microscopy for such studies as NMR allows accurate temperature control and identification of small populations of the LC or isotropic phase.

The data provided in this example illustrate that short β-peptides can serve as mesogens for lyotropic LC phase formation in water. The example studied most carefully, deca-β-peptide 3, forms a cholesteric phase at room temperature. In this example, liquid crystallinity appears to require the adoption of a globally amphiphilic conformation, because sequence isomer 5 does not display LC behavior. LC phase behavior of 3 is modulated by concentration and temperature; a change of net charge (Ac-3) resulted in a room temperature LC phase at just 2.5 wt %. At present, LC-forming helical α-peptides that contain so few residues have not been shown to form lyotropic LC phases in water, although nematic LC phases and gels from β-strand-forming α-peptides in this length range are known. Although nematic LCs have been reported to form in systems of α-peptides that assemble into micrometer-sized fibrils over weeks, the timescale of formation of these LC phases is substantially longer than for those reported in this example. Accordingly, β-peptides offer a tunable scaffold for tailoring LC properties for a variety of applications, including, but not limited to, biomolecular sensing applications.

Materials.

Fmoc-(S,S)-trans-2-aminocyclohexanecarboxylic acid (Fmoc-S,S-ACHC) was prepared by the method outlined by Schinnerl et al (*Eur. J. Org. Chem.* 2003, 721) Fmoc-(S)-β³homolysine(Boc)-OH, and Fmoc-(S)-β³homotyrosine(t-Bu)-OH were prepared from their corresponding α-amino-acids (Novabiochem). Biotech grade DMF was purchased from Aldrich and stored over 50W-X8 DOWEX ion-exchange resin. Methanol, $CH_2Cl_2$, tetrahydrofuran, and acetonitrile were purchased from Burdick and Jackson. Fmoc-β-homoglycine, O-benzotriazol-1-yl-N,N,N',N'-tetramethyluronium hexafluorophosphate, and NovaSyn TGR® resin (0.25 mmol/g loading) were purchased from Novabiochem. $iPr_2EtN$ was distilled from calcium hydride. All other reagents were purchased from Aldrich and used without purification.

RP-HPLC (Reverse Phase-High Pressure Liquid Chromatography)

All β-peptides were purified via RP-HPLC on a Vydac C18 semipreparative column using a flow rate of 3 mL/min. Solvent A and Solvent B for RP-HPLC were 0.1% trifluoroacetic acid (TFA) in Millipore water and 0.1% TFA in acetonitrile, respectively. β-peptide purity was assessed using a Vydac C18 analytical column using a flow rate of 1 mL/min from 10-60% B over 50 minutes monitoring at 220 and 273 nm. MALDI-TOF-MS (matrix-assisted laser desorption-ionization-time-of-flight mass spectrometry) data were collected on a Bruker REFLEX II spectrometer with a 337 nm laser using α-cyano-4-hydroxycinnamic acid as matrix. Measurements were calibrated using peptide standards angiotensin I $(M+H^+)=1296.7$ and neurotensin $(M+H^+)=1672.9$.

Optical Microscopy

β-Peptides were weighed into glass vials, diluted to the desired concentration with water, and left on an oscillatory shaker overnight to ensure dissolution. β-peptide solutions were then drawn into a 2 μL microcapillary (Drummond), and the ends were sealed with a high viscosity vacuum grease (Dow-Corning) Microcapillaries were placed on a glass slide and imaged on an Olympus BX-60 microscope (Tokyo, Japan) in transmission mode between crossed polarizing filters using a digital camera (Olympus C2020 Zoom). For variable temperature experiments, microcapillary samples were placed on a HCS61 hot stage from Instec Inc., and heated in 1 degree increments every ten minutes. Temperature was recorded from a thermostat but was not further calibrated.

$^2H$ NMR Phase Studies of Lyotropic Liquid Crystal 3

To characterize the temperature-dependent phase behavior, a 10 wt % solution of β-peptide 3 was prepared in $D_2O$ (99.9% D, Cambridge Isotope Laboratories, Inc.). After dissolution, the sample was transferred to a 3 mm NMR tube (Wilmad) and placed in a 500 mHz Varian NMR spectrometer. Spectra of $D_2O$ were recorded in 1 degree increments allowing 10 minutes for equilibration between scans. Sample temperature was calibrated using an ethylene glycol standard according to published methods.

General Procedure for the Microwave-Assisted Solid Phase Synthesis of β-Peptides.

All 14-helical β-peptides were synthesized on solid phase in a CEM MARS microwave reactor. Microwave irradiation used a maximum power of 600 W. Reaction mixtures were agitated by magnetic stirring during irradiation. Reaction temperature was monitored using a fiberoptic temperature sensor. Coupling and deprotections used the following conditions: couplings: (600 W maximum power, 80° C., ramp 2 minutes, hold 4 minutes); deprotections: (600 W maximum power, 90° C., ramp 2 minutes, hold 2 minutes). For difficult couplings an additional temperature ramping cycle was included: (600 W maximum power, 80° C.; ramp 2 minutes, 0 W, 25° C.; 10 minutes hold, 3×).

Representative Example of Microwave-Assisted Synthesis of β-peptide (3).

β-peptide 3 was synthesized on a 10 μmol scale on NovaSyn TGR® resin in a microwave reactor (CEM, MARS system). All coupling and deprotection reactions were carried out at atmospheric pressure under microwave irradiation as described above. Prior to coupling, the resin was swelled in $CH_2Cl_2$ for 20 minutes in a solid phase extraction tube (Altech). The resin was washed 3 times with DMF. In a separate vial, Fmoc-β-amino acid (30 μmol) was dissolved in 440 μL of DMF and activated with O-benzotriazol-1-yl-N,N,N',N'-tetramethyluronium hexafluorophosphate (HBTU, 60 μL of 0.5 M solution in DMF), 1-hydroxybenzotriazole monohydrate (HOBT, 60 μL of 0.5 M solution in DMF), and $iPr_2EtN$ (60 μL of 1.0 M solution in DMF). The coupling solution was vortexed, added to the resin, and the mixture was irradiated at 80° C. as described above. The resin was washed (3× DMF, 3× $CH_2Cl_2$, and 3× DMF). Deprotection solution (750 μL of 20% piperidine in DMF (v/v)) was added to the resin, and the mixture was irradiated at 90° C. and washed as before. All ACHC residues were double-coupled and double-deprotected. Difficult coupling reactions for ACHC-2 and ACHC-5 were subjected to the temperature ramping cycle immediately following the second coupling. The coupling/deprotection cycles were repeated until the $10^{th}$ residue. The β-peptide was cleaved from the resin in a mixture of 95/2.5/2.5 TFA/$H_2O$/triisopropylsilane for 2 hr, followed by evaporation of the solvent under a nitrogen stream. The crude β-peptide was then purified by RP-HPLC and lyophilized to yield a white powder.

β-peptide 3: RP-HPLC purification: 35-45% B over 20 min. MALDI-TOF-MS (m/e) calculated for ($C_{73}H_{122}N_{14}O_{11}$; M=1370.9); found: $(M+H^+)=1371.8$; $(M+Na^+)=1393.8$; $(M+K^+)=1409.8$.

β-peptide 1: RP-HPLC purification: 0-30% B over 30 min. MALDI-TOF-MS (m/e) calculated for ($C_{31}H_{50}N_6O_5$; M=586.4); found: $(M+H^+)=587.2$; $(M+Na^+)=609.2$; $(M+K^+)=625.1$.

β-peptide 2: RP-HPLC purification: 26-36% B over 20 min MALDI-TOF-MS (m/e) calculated for ($C_{52}H_{86}N_{10}O_8$; M=978.7); found: $(M+H^+)=979.9$; $(M+Na^+)=1001.9$; $(M+K^+)=1017.9$ β-peptide Ac-3: Following final deprotection, acetylation of the N-terminus was achieved by agitating the resin with 2 mL of a $CH_2Cl_2$/TEA/acetic anhydride solution 1.4/0.1/0.5 (v/v/v) for 2 hrs. followed by washing the resin with $CH_2Cl_2$ 3 x. β-Peptide was cleaved from the resin in a mixture of 95/2.5/2.5 TFA/$H_2O$/triisopropylsilane for 2 hr, followed by evaporation of the solvent under a nitrogen stream. The crude β-peptide was then purified by RP-HPLC and lyophilized to yield a white powder.

RP-HPLC purification: 35.5-45.5% B over 20 min. MALDI-TOF-MS (m/e) calculated for ($C_{75}H_{124}N_{14}O_{12}$; M=1412.95); found: (M+H$^+$)=1413.7; (M+Na$^+$)=1435.7; (M+K$^+$)=1451.8.

β-peptide 4: RP-HPLC purification: 46-56% B over 20 minutes MALDI-TOF-MS (m/e)calculated for ($C_{94}H_{158}N_{18}O_{14}$; M=1764.2); (M+H$^+$)=1764.1; (M+Na$^+$)=1786.1; (M+K$^+$) =1802.1

β-peptide 5: RP-HPLC purification: 21-31% B over 20 min. MALDI-TOF-MS (m/e) calculated for ($C_{73}H_{122}N_{14}O_{11}$; M=1370.9); (M+H$^+$)=1372.1 (M+Na$^+$)=1394.1 (M+K$^+$)=1802.1

Referring now to FIG. 6, optical micrographs of aqueous solutions of beta-peptides derived from 3 are provided. From left to right, a hydrophobic scan of 3 indicates that the deletion of the N terminal β$^3$-hTyr group, or the substitution of β$^3$-hVal, β$^3$-hLeu or β$^3$-hPhe for an ACHC residue in 3 results in an analog beta-peptide unable to form a liquid crystal phase.

Figure 7:
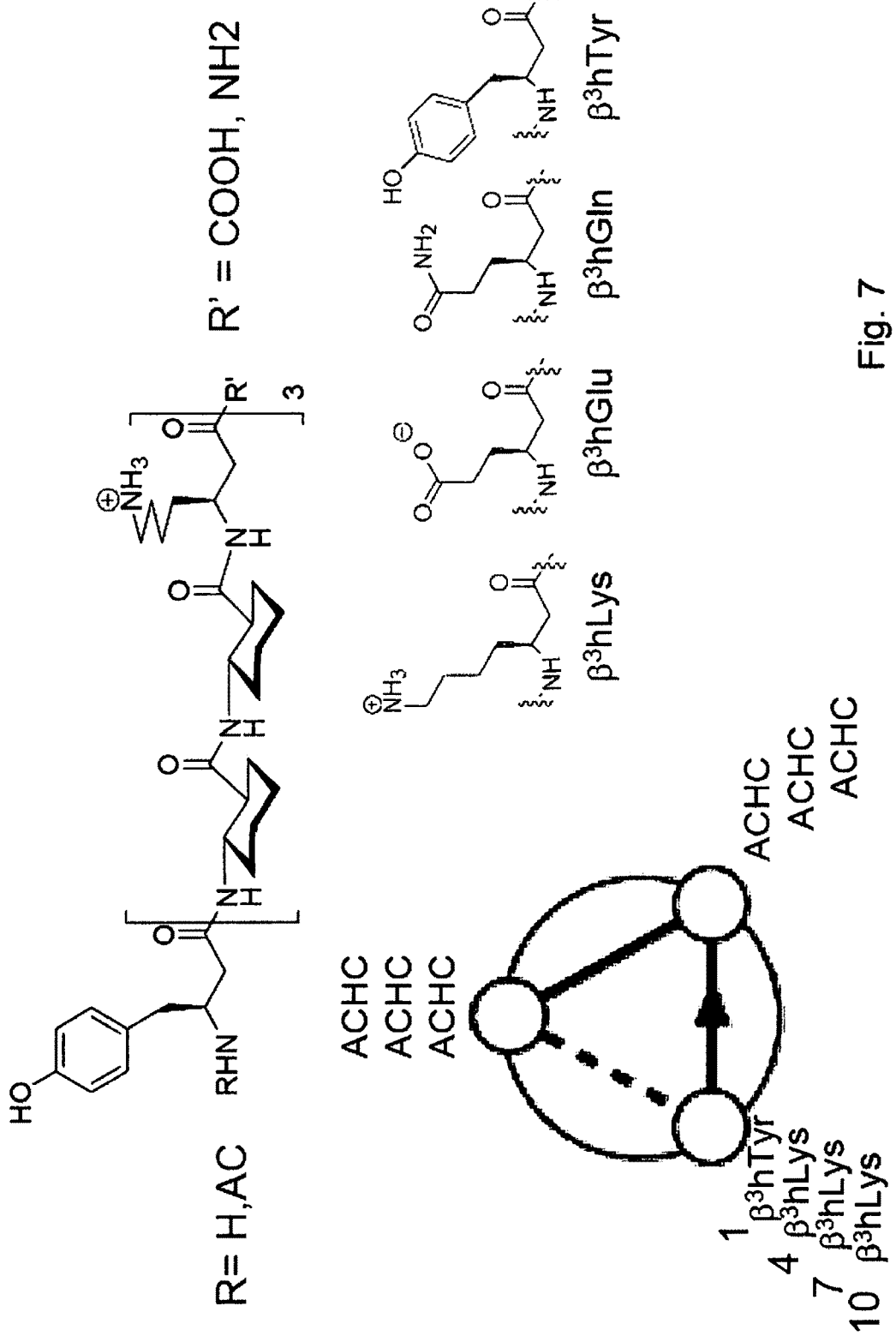
FIG. 7 illustrates various hydrophilic analogs of 3, substituted at the N terminal β$^3$-hTyr or β$^3$-hLys 4, 7 or 10 positions with the indicated hydrophilic residues.
Figure 8:
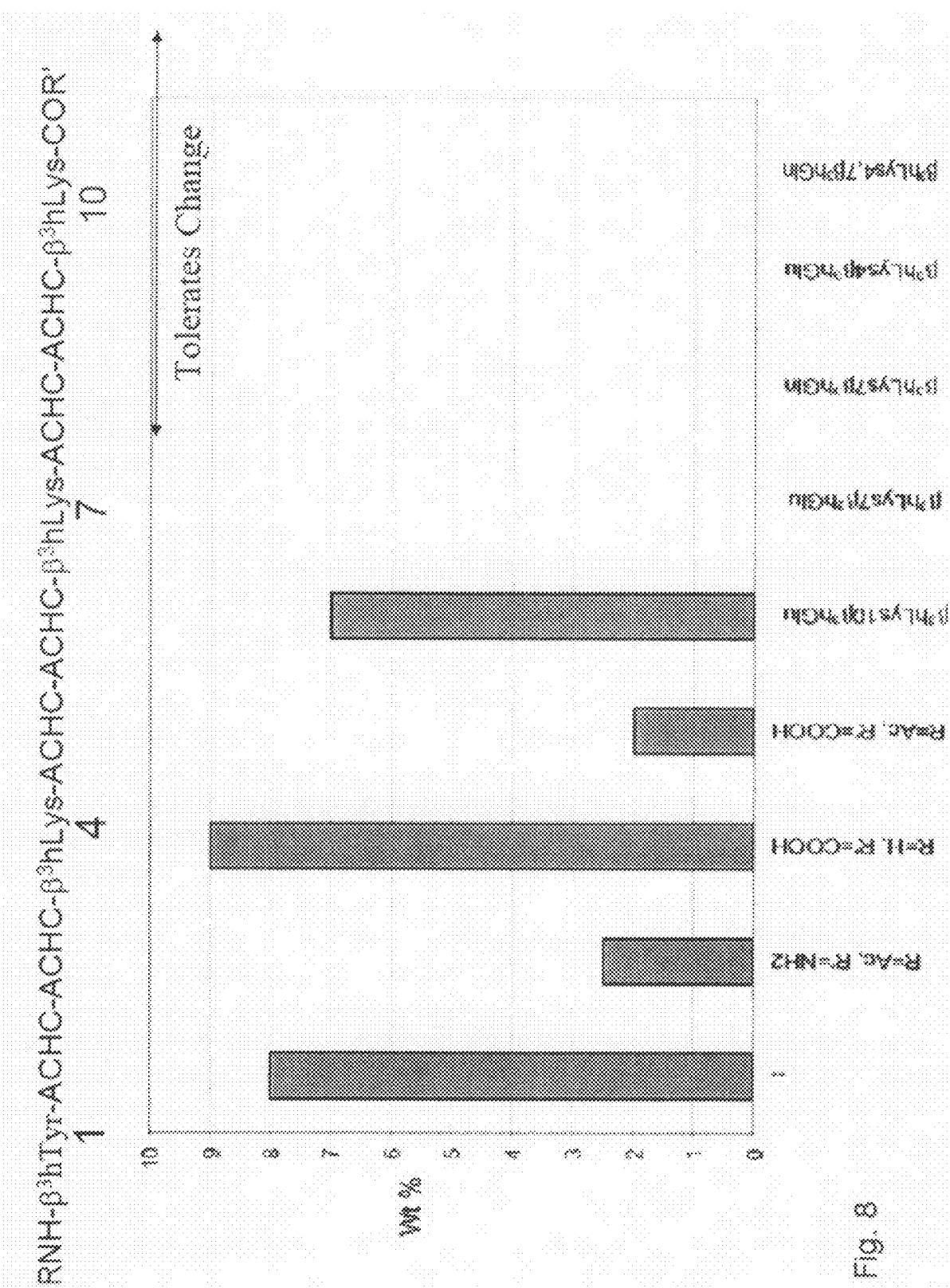
FIG. 8 provides optical micrographs of aqueous solutions of beta-peptides shown in FIG. 7 derived from 3 between crossed polarizing filters.

FIG. 7 illustrates various hydrophilic analogs of 3, substituted at the N terminal β3-hTyr or β$^3$-hLys 4, 7 or 10 positions with the indicated hydrophilic residues. Related FIG. 8 provides optical micrographs of aqueous solutions of beta-peptides derived from 3 to include the hydrophilic residues shown in FIG. 7. The data indicate that, in general, 3 tolerates hydrophilic substitutions at its C terminus. Note that substitutions at the 4 and 7 position result in analog beta-peptides unable to form a liquid crystal phase.

Figure 9:
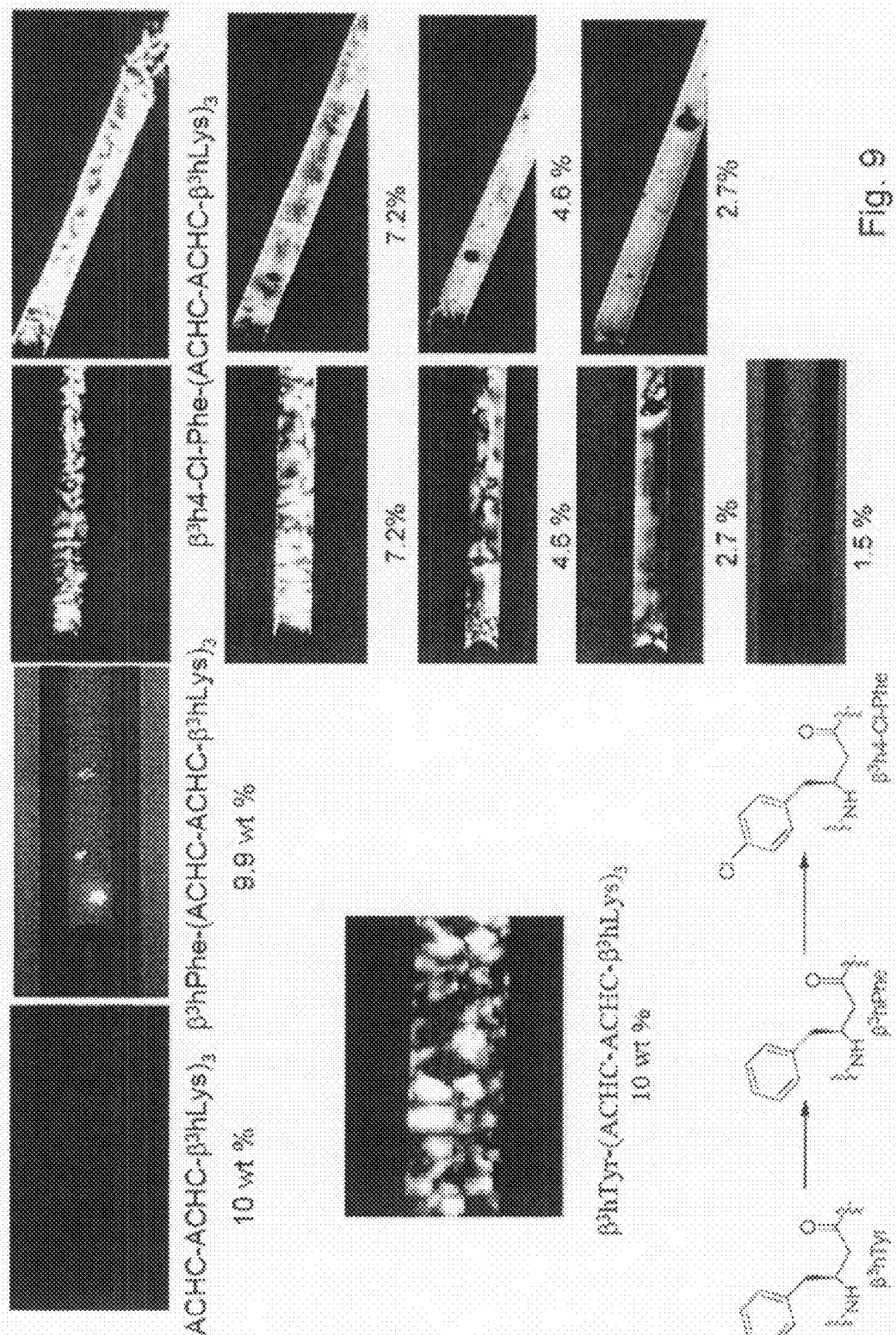
FIG. 9 depicts optical micrographs of aqueous solutions of beta-peptides derived from 3 between crossed polarizing filters that substituted β$^3$-hPhe or β$^3$-h-para-Cl-Phe for the β$^3$-hTyr residue at the N terminus of 3.

Referring now to FIG. 9, optical micrographs are provided of aqueous solutions of beta-peptides derived from 3 that substitute β$^3$-hPhe or β$^3$-h-para-Cl-Phe for the β$^3$-h-Tyr residue at the N terminus of 3. The data indicate removal of the β$^3$-h-Tyr residue results in a beta-peptide unable to form a LC phase at 10 wt %. Substitution by β$^3$-h-Phe results in reduced LC phase formation at 10 wt % as compared to 3. Substitution by β$^3$-h-para-Cl-Phe in the β$^3$-hLys10$^3$-hGlu analog provides the result of improved LC formation at a wt % of only 2.7%.

While no one theory of operation is adopted herein, LC phase formation is made favorable in the case of amphiphilic beta-peptides by: (a) the inclusion of ACHC; (b) removal of +/+ repulsion; and (c) the presence of polar aromatic groups at a beta-peptide's N terminus (e.g., β$^3$-hTyr or β$^3$-h-para-Cl-Phe).

Example 2

Non-Globally Amphiphilic Beta-Peptide Lyotrophic Liquid Crystals I

Figure 10:
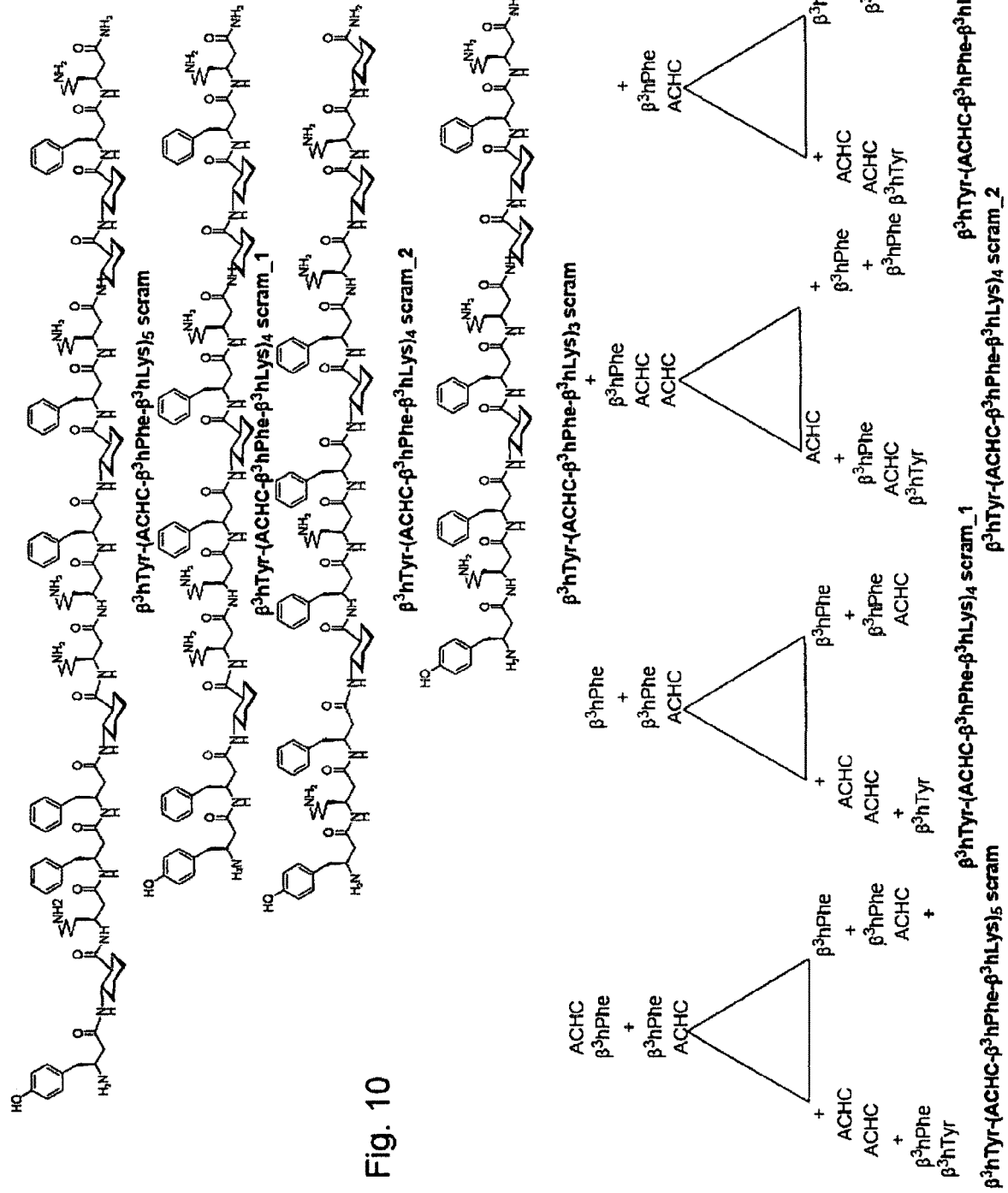
FIG. 10 illustrates various beta-peptides in which the components ACHC, β$^3$-hPhe, and β$^3$-hLys have been scrambled. Helical wheel diagrams for the four analogs are provided and illustrate the partitioning of charge and hydrophobicity around the helices.
Figure 11:
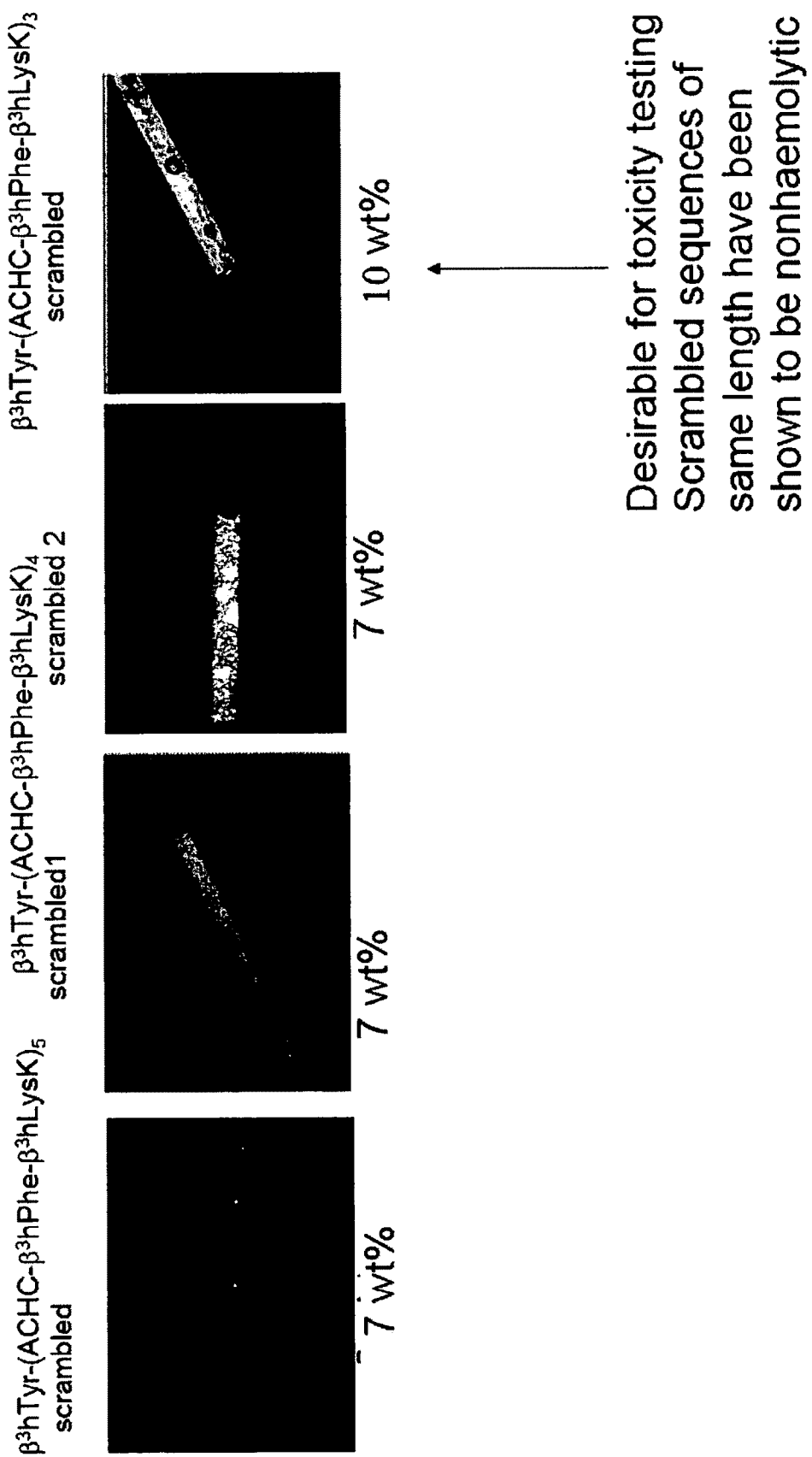
FIG. 11 depicts optical micrographs of aqueous solutions of the beta-peptides shown in FIG. 10 between crossed polarizing filters. Analogs β$^3$-hTyr-(ACHC-β$^3$-hPhe-β$^3$-hLys)$_4$ scrambled 2 and β$^3$-hTyr-(ACHC-β$^3$-hPhe-β$^3$-hLys)$_3$ scrambled display strong birefringence.

Referring now to FIG. 10, various beta-peptides in which the components ACHC, β$^3$-hPhe, and β$^3$-hLys have been scrambled are illustrated. Helical wheel diagrams for the four analogs are provided to aid in visualizing the partitioning of charge and hydrophobicity around the helices. FIG. 11 depicts optical micrographs of aqueous solutions of the beta-peptides shown in FIG. 10 between crossed polarizing filters. Analogs β$^3$-hTyr-(ACHC-β$^3$-hPhe-β$^3$-hLys)$_4$ scrambled 1 ("scram1"), β$^3$-hTyr-(ACHC-β$^3$-hPhe-β$^3$-hLys)$_4$ scrambled 2 ("scram2"), and β$^3$-hTyr-(ACHC-β$^3$-hPhe-β$^3$-hLys)$_3$ scrambled ("scram") display strong birefringence.

Figure 13:
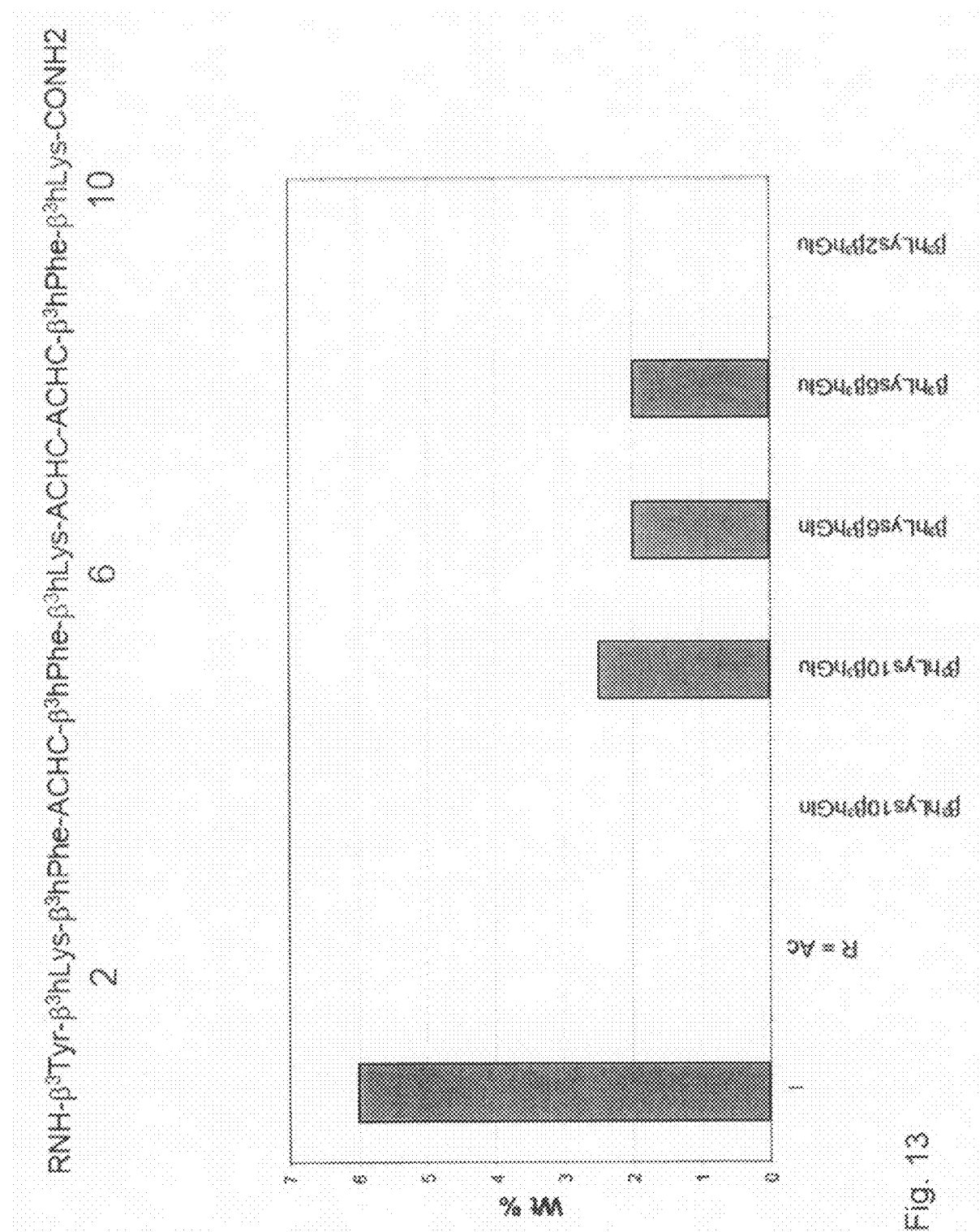
FIG. 13 illustrates a plot of the wt % of the various analog beta-peptides of FIG. 12 necessary to form a liquid crystal phase at room temperature.

Referring now to FIG. 12, various analog beta-peptides based on β$^3$-hTyr-(ACHC-β$^3$-hPhe-β$^3$-hLys)$_3$ are illustrated. Hydrophilic substitutions of β$^3$-hGlu and β$^3$-hGln residues were made at β$^3$-hLys position 2, 6 of 10 of β$^3$-hTyr-(ACHC-β$^3$-hPhe-β$^3$-hLys)$_3$. FIG. 13 illustrates a plot for these hydrophilic analog beta-peptides indicating the wt % necessary to form a liquid crystal phase at room temperature. Hydrophilic substitutions at positions 6 and 10 were tolerated but substitution at position 2 resulted in an analog unable to form an LC phase at low wt %.

Example 3

Non-Globally Amphiphilic Beta-Peptide Lyotrophic Liquid Crystals II

Figure 14:
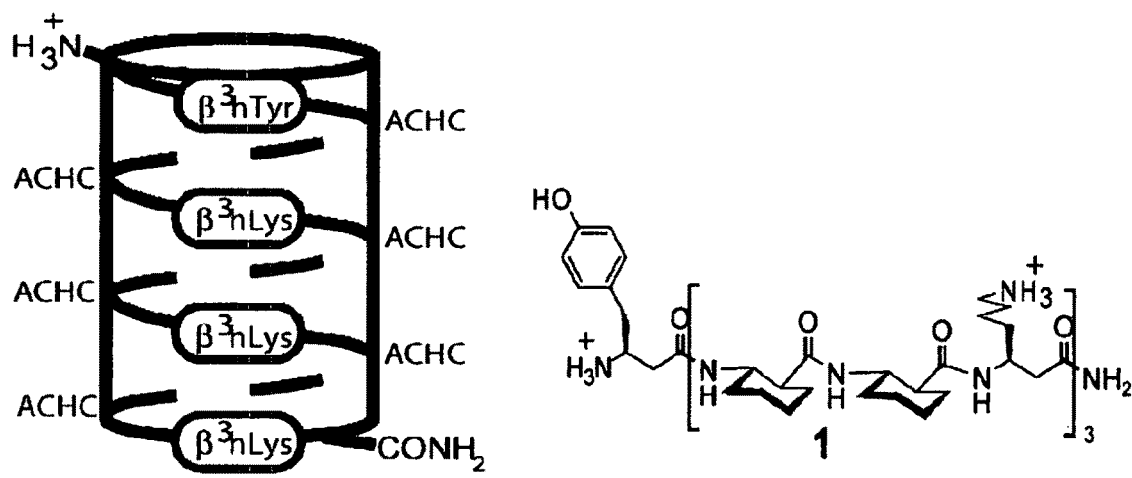
FIG. 14 depicts a previously characterized β-Peptide 1, cylinder representation (Left) and sequence (Right).

The inventors have identified that properly designed β-peptides, such as the one shown in FIG. 14, could form LC phases in aqueous solution. This β-peptide was intended to be globally amphiphilic in the preferred 14-helical conformation (this helix is defined by 14-membered ring N—H$_i$→O═C$_{i+2}$ hydrogen bonds between backbone amide groups). The 14-helix has approximately three residues per turn; therefore, sequences such as 1, containing a lipophilic-lipophilic-hydrophilic triad repeat adopt helical conformations in which lipophilic side chains are globally segregated on one side of the helix and hydrophilic side chains are globally segregated the other side (FIG. 14). Isomeric sequences lacking the triad repeat pattern cannot achieve this global segregation of lipophilic and hydrophilic side chains. The inventors' design hypothesis was that extended lipophilic surfaces displayed by folded β-peptides would give rise to a hydrophobic driving force for assembly in aqueous solution. The success of this design was indicated by the observation that β-peptide 1 forms a LC phase while a sequence isomer that cannot form a globally amphiphilic helix is unable to self-assemble and does not form a LC phase.

In this example, the inventors report the unexpected discovery of a series of β-peptides that cannot form a globally amphiphilic helix but that are nevertheless capable of forming LC phases in water. This finding expands the range of β-peptide sequences that can be harnessed as mesogens.

Figure 15:
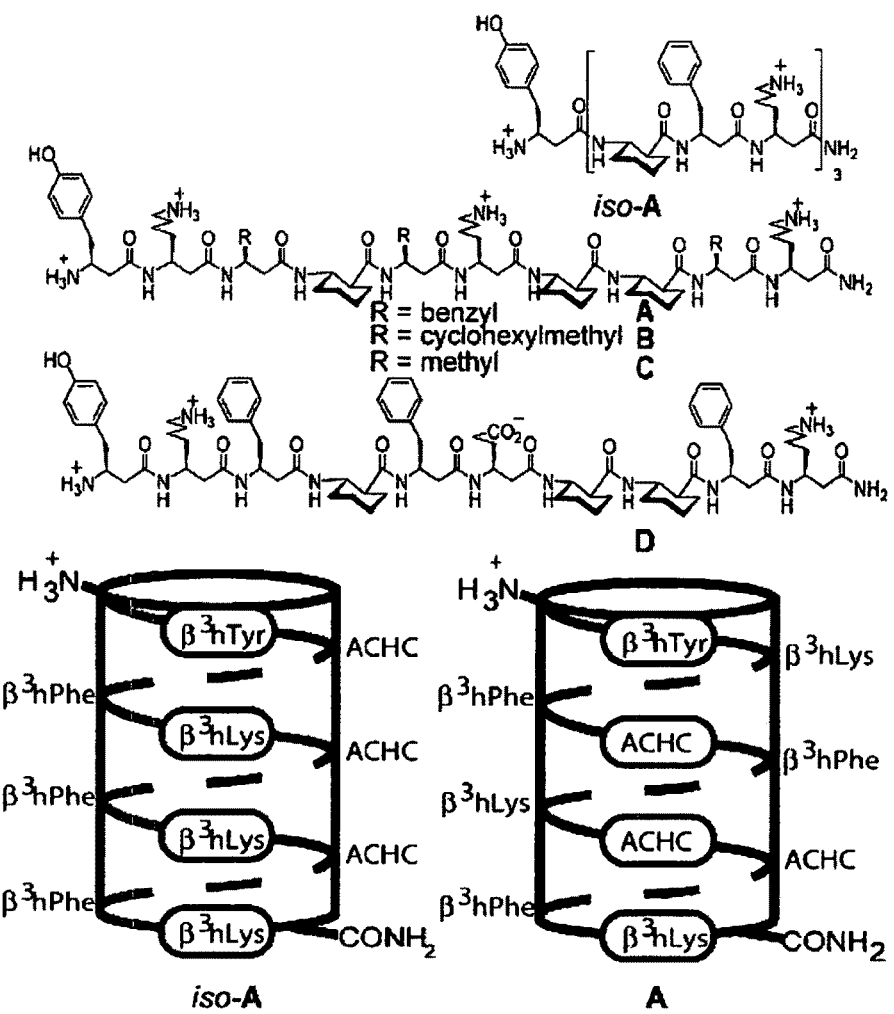
FIG. 15 shows β-Peptide sequences (top) and cylinder representations of non-globally amphiphilic A and globally amphiphilic iso-A(bottom).
Figure 16:
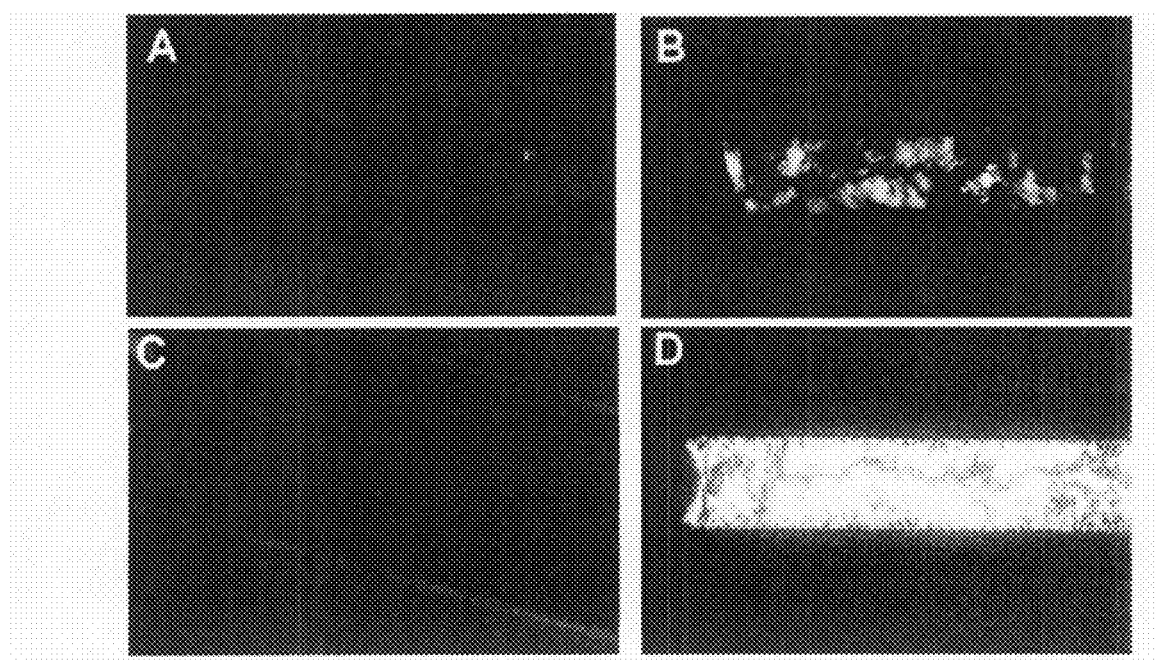
FIG. 16 provides optical micrographs of solutions of β-peptides between crossed polarizing filters A) iso-A, 10 wt %, B) A, 10 wt % C) B 9 wt % D) D, 4 wt %.

Initial efforts focused on sequence isomers A and iso-A. The latter has a repeating triad motif containing trans-2-aminocyclohexanecarboxylic acid (ACHC), β$^3$homophenylalanine (β$^3$hPhe) and β$^3$hLys residues; the ACHC-β$^3$hPhe-β$^3$hLys repeat has the lipophilic-lipophilic-hydrophilic pattern previously found to lead to LC phase formation in aqueous solution (e.g., 1). In contrast, the sequence of A is such that 14-helical folding does not lead to a global segregation of lipophilic and hydrophilic side chains, but rather to distribution of lipophilic and hydrophilic side chains around the entire periphery of the helix (FIG. 15). In light of previous results, the inventors expected iso-A to form a LC phase in water, and for A not to form a LC phase, but optical microscopy revealed the opposite trend (FIG. 16). Strong birefringence was observed for aqueous solutions containing ≧6.5 wt % A, but no birefringence was detected for solutions of iso-A up to the solubility limit (>10 wt %). The aromatic side chains of the β$^3$hPhe residues are necessary for LC phase formation by A, because replacing each aromatic ring with a cyclohexyl ring (B) or removing the aromatic rings altogether (C) abolished LC phase formation. Lowering the net charge on the β-peptide mesogen, by replacing β$^3$hLys-6 with β$^3$hGlu, to form D, allowed LC phase formation at concentrations as low as 2 wt %. This finding suggests that electrostatic forces between β-peptide molecules has a large effect on LC phase formation. In addition, the effect of this "point mutation" on LC behavior illustrates the ease with which the covalent structure and pattern of side chain display can be altered among β-peptide mesogens.

Figure 17:
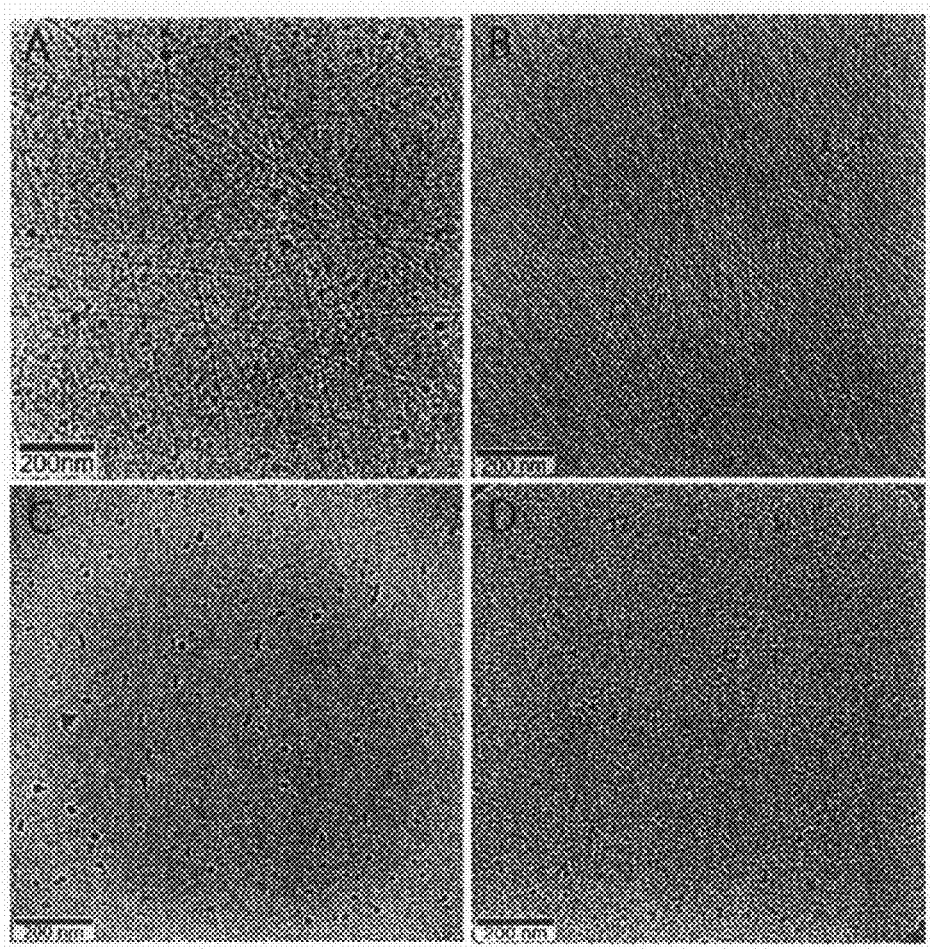
FIG. 17 provides cryo-TEM micrographs of A and iso-A A) A, 2 wt %, B) A, 8 wt %, C) iso-A, 2 wt % and D) iso-A, 8 wt %.

The inventors suspected that LC phase formation requires β-peptide self-association, i.e., that the true mesogen in these systems is an aggregated form of the β-peptide. Onsager theory predicts that mesogens with a high aspect ratio will spontaneously form LC phases at a critical concentration through an entropy-driven process. This theory requires large aggregates (>500 monomers) if LC behavior is observed at concentrations as low as 2 wt %. Cryogenic-transmission electron microscopy (cryo-TEM) was undertaken in an effort to obtain further evidence for formation of high aspect ratio assemblies in lyotropic LC phases formed by β-peptides. At 2 wt % A, below the concentration required for LC phase formation, cryo-TEM revealed micron-long fibers intermixed with smaller globular aggregates (FIG. 17A). At 8 wt % A, which forms a lyotropic LC phase, a densely packed network of fibers was observed (FIG. 17B). Nanoscale assemblies of this type could correspond to the high aspect ratio mesogens predicted by Onsager theory which suggests that nanofibers generated by β-peptide self-assembly serve as the mesogenic species for LC phase formation. Only globular aggregates were observed in aqueous solutions of iso-A over the concentration range studied, consistent with the inability of this β-peptide to support lyotropic LC phase formation (FIG. 17C,D). These conclusions are supported by small angle X-ray scattering (SAXS) experiments.

Figure 18:
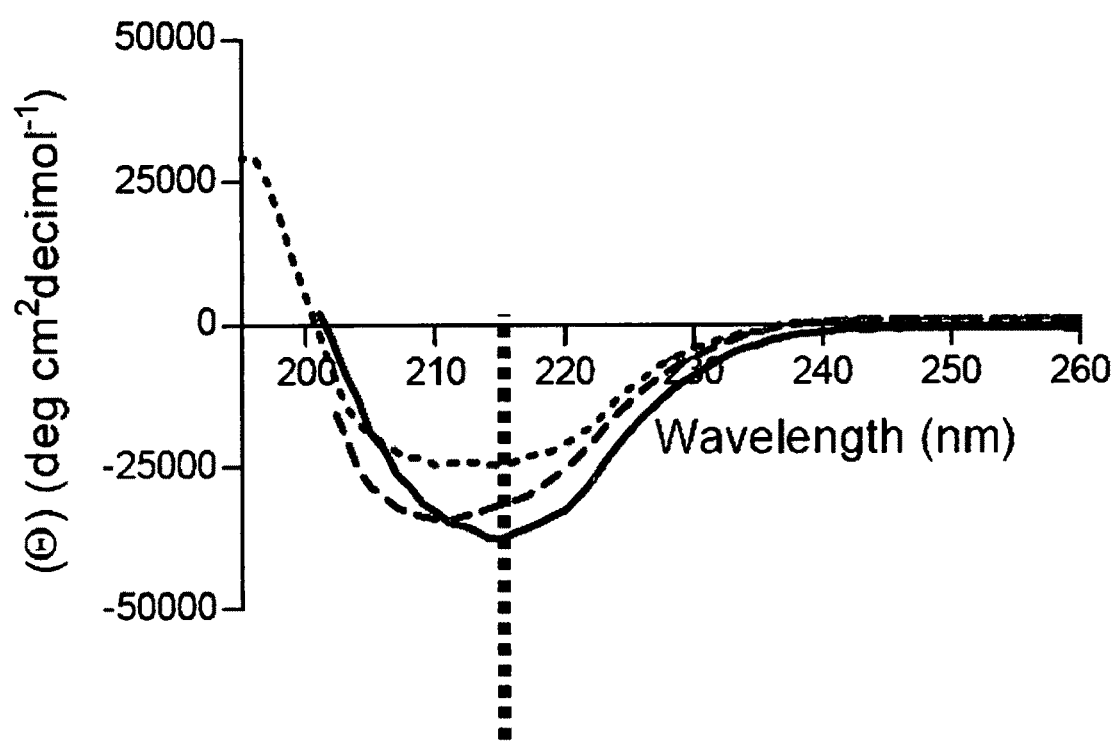
FIG. 18 provides circular dichroism spectra of β-peptides A (2 wt %; solid line), iso-A (2 wt %; long dash line), and D (0.8 wt %; short dash line). Minimum at 214 nm is indicated with a dashed line.

The inventors undertook circular dichroism (CD) measurements to determine whether β-peptides of the type discussed here remain 14-helical under conditions approaching those required for nanofiber formation. It was previously shown that α-helical α-peptides can denature to form β-sheets that aggregate at high concentration, and, also, β-sheet assemblies can form LC phases. β-Peptide D was analyzed at 0.8 wt %, which just below the minimum LC concentration (birefringence arising from LC phase formation interferes with the CD measurement). The inventors observe a broad minimum near 214 nm in the CD spectrum for β-Peptide D (short dash line), which is characteristic of the 14-helix (FIG. 18). A similar minimum was observed for a 0.05 wt % (0.27 mM) sample of D. The lack of variation in the CD signature over this concentration range suggests that D remains 14-helical under conditions near those required for LC phase formation. β-Peptides A (solid line) and iso-A (long dash line) displayed strong 14-helical signatures up to 2 wt %, the concentration where nanofibers begin to form for A. These β-peptides could not be analyzed by CD at higher concentrations due to the high absorption of light by the amide chromophore, which results in loss of signal. Overall, the data indicate that both A and D display 14-helicity even at relatively high concentrations, which is consistent with the strong 14-helix propensity of ACHC residues. These results suggest that nanofiber formation results from self-assembly of β-peptides in the 14-helical conformations In conclusion, the inventors have discovered a new family of helical β-peptides that support lyotropic liquid crystalline phase formation. These molecules adopt conformations that are not globally amphiphilic in the folded state. This behavior runs counter to the trend we previously documented among β-peptides containing a higher proportion of ACHC residues, in which the non-globally amphiphilic isomer did not assemble or form a liquid crystalline phase. These seemingly contradictory observations are reconciled through consideration of the nanostructures formed by the β-peptides where cryo-TEM data indicates that LC phase formation depends upon the ability of the β-peptide to assemble into nanofibers. β-Peptide iso-A self-associates in aqueous solution, but in this case the globular shape of the assemblies does not promote LC phase formation. The inventors' findings are consistent with Onsager theory, because the data indicate that nanofibers, with high aspect ratios, serve as the mesogenic agents.

Materials and Methods

Materials. Fmoc-(S,S)-trans-2-aminocyclohexanecarboxylic acid (Fmoc-S,S-ACHC) was prepared by the method outlined by Schinnerl et al. (Schinnerl, M.; Murray, J. K.; Langehan, J. M.; Gellman, S. H. *Eur. J. Org. Chem.* 2003, 721-6.). Fmoc-(S)-$β^3$-amino acids were prepared from their corresponding a-amino-acids (Novabiochem),[2] or purchased from Peptech. Biotech grade DMF was purchased from Aldrich and stored over 50W-X8 DOWEX ion-exchange resin. Methanol, $CH_2Cl_2$, tetrahydrofuran, and acetonitrile were purchased from Burdick and Jackson. O-benzotriazol-1-yl-,N,N,N',N'-tetramethyluronium hexafluorophosphate, and NovaSyn TGR® resin (0.25 mmol/g loading) were purchased from Novabiochem. $iPr_2EtN$ was distilled from calcium hydride. All other reagents were purchased from Aldrich and used without purification.

RP-HPLC (Reverse Phase-High Pressure Liquid Chromatography)

All β-peptides were purified via RP-HPLC on a Vydac C 18 semipreparative column using a flow rate of 3 mL/min. Solvent A and Solvent B for RP-HPLC were 0.1% trifluoroacetic acid (TFA) in Millipore water and 0.1% TFA in acetonitrile, respectively. β-peptide purity was assessed using a Vydac C18 analytical column using a flow rate of 1 mL/min from 10-60% B over 50 minutes monitoring at 220 and 273 nm.

MALDI-TOF-MS (matrix-assisted laser desorption-ionization-time-of-flight mass spectrometry) data were collected on a Bruker REFLEX II spectrometer with a 337 nm laser using α-cyano-4-hydroxycinnamic acid as matrix. Measurements were calibrated using peptide standards angiotensin I $(M+H^+)$=1296.7 and neurotensin $(M+H^+)$=1672.9.

Optical Microscopy

β-Peptides were weighed into eppindorf tubes, diluted to the desired concentration with water, and left on an oscillatory shaker overnight to ensure dissolution. β-peptide solutions were then drawn into a 2 μL microcapillary (Drummond), and the ends were sealed with a high viscosity vacuum grease (Dow-Corning) Microcapillaries were placed on a glass slide and imaged on an Olympus BX-60 microscope (Tokyo, Japan) in transmission mode between crossed polarizing filters using a digital camera (Olympus C2020 Zoom). To assess the upper limit of concentration, a 1 μL droplet of a concentrated peptide solution was allowed to slowly evaporate while being monitored for birefringence.

Circular Dichroism (CD) Analysis

Samples were prepared by weighing lyophilized β-peptides into Eppendorf tubes and dissolving in Millipore water to yield a 2 wt % solution which was aliquoted and further diluted to the desired concentrations. The final concentration of each β-peptide solution was determined from the UV absorbance of a solution of known dilution. The extinction coefficient of each β-peptide at 275 nm was estimated to be 1420 $cm^{-1}$ $mol^{-1}$, based on the extinction coefficient of α-tyrosine. Circular dichroism spectra were recorded on an Aviv 202SF spectrometer at room temperature using a 1 mm path, 0.1 mm, or 0.01 mm path length cell and 3 second averaging times. The CD signal resulting from the water alone was subtracted from the spectrum of each β-peptide solution. Data were converted to ellipticity (deg $cm^2$ $dmol^{-1}$) according to the equation: $[Θ]=Ψ/(1000 nlc)$, where Ψ is the CD signal in degrees, n is the number of amides, l is the path length in centimeters, and c is the concentration in decimoles per $cm^3$.

Cryo-Transmission Electron Microscopy (TEM)

A small quantity of the sample solution was applied to a holey carbon grid and blotted with filter paper to create a thin layer of sample on the surface of the grid. The grid was plunged into liquid ethane and quickly transferred to liquid nitrogen. The sample was analyzed under JEOL 2010 TEM at an accelerating voltage of 200 kV.

Fluorescence Imaging of Biotin Bound Streptavidin on Gold Substrates

Alkane thiol solutions were prepared by dissolving HS—$(CH_2)_{10}$COOH or HS—$(CH_2)_6$—OH in ethanol to a final concentration of 2 mM. Gold slides of composition 100 nm Au with a base layer of 10 nm Ti, were then incubated in a 1:1 mixture of thiol solutions overnight. After rinsing thoroughly with ethanol and water, the resulting gold chips with self-assembled monolayers were immersed in an aqueous solution of 1-ethyl-3-3(3-dimethylaminopropyl-carbodiimide (EDC (200 mM) and N-hydroxysuccinimide (NHS, 50 mM) for 10 minutes to generate activated succinimidyl esters in situ. 20 µL of a streptavidin solution (Pierce Biotechnology, 10 µM, pH 6.5, 10 mM phosphate) was applied to the surface of each gold chip and allowed to incubate for 4 hrs in a Petri dish with a water saturated piece of filter paper to prevent evaporation. Following incubation chips were again rinsed with water and placed in a basic aqueous solution (pH 8.6, 10 mM phosphate) to hydrolyze any unreacted activated ester. Slides were then overlaid with 20 µL of either a 1) pH 6.5, 50 mM phosphate aqueous solution, positive control for non-denaturing conditions 2) 16 wt % disodium chromoglycate (DSCG), a positive control for non-denaturing conditions with a liquid crystal 3) 32 wt % of sodium decyl sulfate, (SDeS) a negative control for non-denaturing conditions with a liquid crystal and 4) an experimental liquid crystal. Slides were incubated for 2 hrs and then washed with water. Finally slides were spotted with 1 uL of a 10 uM solution of Alexafluor594-Biotin (Invitrogen) and incubated for 2 hrs. Excess dye was removed by soaking gold chips in an aqueous solution, (pH 6.5 10 mM phosphate) for 10 minutes, followed by rinsing with water and then ethanol and finally and drying under a stream of with nitrogen. Biotin bound streptavidin was imaged by scanning with a Geneomic Solutions Genetac UC4×4 Fluoescence scanner.

General Procedure for the Microwave-Assisted Solid Phase Synthesis of β-Peptides.

All 14-helical β-peptides were synthesized on solid phase in a CEM MARS microwave reactor. Microwave irradiation used a maximum power of 600 W. Reaction mixtures were agitated by magnetic stirring during irradiation. Reaction temperature was monitored using a fiberoptic temperature sensor. Coupling and deprotections used the following conditions: couplings: (600 W maximum power, 80° C., ramp 2 minutes, hold 4 minutes); deprotections: (600 W maximum power, 90° C., ramp 2 minutes, hold 2 minutes). For difficult couplings[4] an additional temperature ramping cycle was included: (600 W maximum power, 80° C.; ramp 2 minutes, 0 W, 25° C.; 10 minutes hold, 3×).

Representative Example of Microwave-Assisted Synthesis of β-peptide (A).

β-peptide A was synthesized on a 10 µmol scale on NovaSyn TGR® resin in a microwave reactor (CEM, MARS system). All coupling and deprotection reactions were carried out at atmospheric pressure under microwave irradiation as described above. Prior to coupling, the resin was swelled in $CH_2Cl_2$ in a solid phase extraction tube (Alltech). The resin was washed 3 times with DMF. In a separate vial, Fmoc-β-amino acid (30 µmol) was dissolved in 400 µL of DMF and activated with O-benzotriazol-1-yl-N,N,N',N'-tetramethyluronium hexafluorophosphate (HBTU, 60 µL of 0.5 M solution in DMF), 1-hydroxybenzotriazole monohydrate (HOBT, 60 µL of 0.5 M solution in DMF), and $iPr_2EtN$ (60 µL of 1.0 M solution in DMF). The coupling solution was vortexed, added to the resin, and the mixture was irradiated at 80° C. as described above. The resin was washed (3× DMF, 3× $CH_2Cl_2$, and 3× DMF). Deprotection solution (750 µL of 20% piperidine in DMF (v/v)) was added to the resin, and the mixture was irradiated at 90° C. and washed as before. All ACHC residues were double-coupled and double-deprotected. Difficult coupling reactions for ACHC-4 was subjected to the temperature ramping cycle immediately following the second coupling. The coupling/deprotection cycles were repeated until the last residue was deprotected. The β-peptide was cleaved from the resin in a mixture of 95/2.5/2.5 TFA/$H_2O$/triisopropylsilane for 2 hr, followed by evaporation of the solvent under a nitrogen stream. The crude β-peptide was then purified by RP-HPLC and lyophilized to yield a white powder.

β-peptide A: 29.5-39.5% B over 20 min. MALDI-TOF-MS (m/e) calculated for ($C_{82}H_{122}N_{14}O_{11}$; M=1479.0); found: $(M+H^+)$=1479.6; $(M+Na^+)$=1501.7.

β-peptide iso-A: 42-52% B over 20 min. MALDI-TOF-MS (m/e) calculated for ($C_{82}H_{122}N_{14}O_{11}$; M=1479.0); found: $(M+H^+)$=1479.7; $(M+Na^+)$=1501.7; $(M+K^+)$=1517.7.

β-peptide B: 34-44% B over 20 min. MALDI-TOF-MS (m/e) calculated for ($C_{82}H_{140}N_{14}O_{11}$; M=1497.08); $(M+H^+)$=1497.7 $(M+Na^-)$=1519.7 $(M+K^+)$=1524.6

β-peptide C: 23-33% B over 20 min. MALDI-TOF-MS (m/e) calculated for ($C_{64}H_{110}N_{14}O_{11}$; M=1250.8); $(M+H^+)$=1251.7 $(M+Na^+)$=1273.7 $(M+K^+)$=1289.9

β-peptide D: 29.5-39.5% B over 20 minutes MALDI-TOF-MS (m/e) calculated for ($C_{81}H_{117}N_{13}O_{13}$; M=1479.9); $(M+H^-)$=1480.9; $(M+Na^+)$=1502.9; $(M+K^+)$=1518.9; $(M+2Na^+)$=1524.9

Example 4

Figure 19:
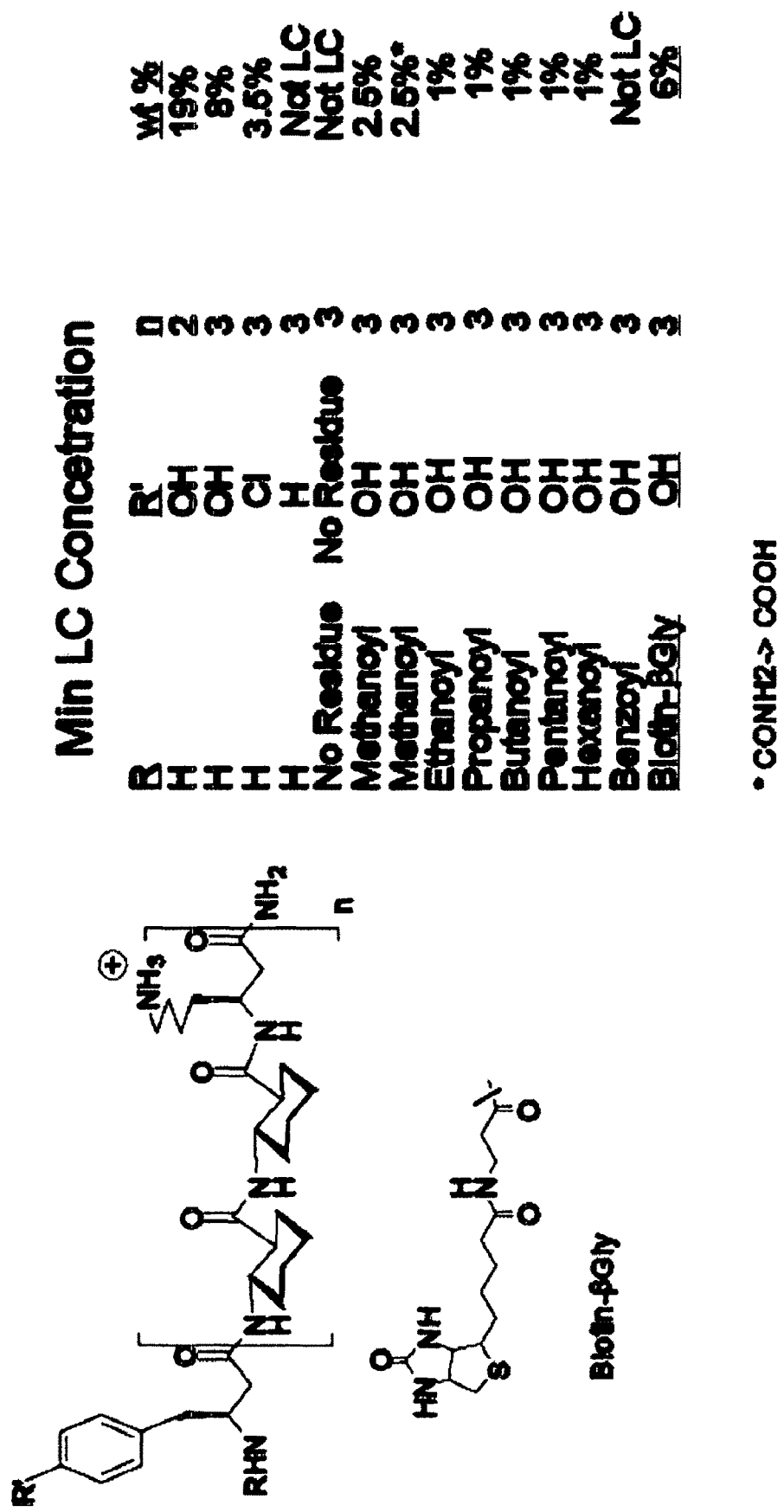
FIG. 19 shows a summary of β-peptide sequences and their respective minimum liquid crystalline forming concentrations. All derivatives were based upon the general sequence X-(ACHC-ACHC-β$^3$hLys)$_3$.

Additional Globally Amphiphilic Beta-peptide Lyotropic Liquid Crystals Including Functionalized Variant The flexibility in design of new lyotropic liquid crystals using globally amphiphilic β-peptides of the general sequence RNH-X-(ACHC-ACHC-$β^3$-hLys)$_3$ is illustrated in FIG. 19. For these sequences X refers to a $β^3$-amino acid containing a benzylic side chain. Results from this study revealed that changing the aromatic residue of parent β-peptide 3, R═H, X═OH; to X═Cl resulted in a reduction in the minimum LC concentration (entry 3). However, removal of the phenolic hydroxyl group, (X═H, entry 4), or the aromatic ring altogether (entry5) resulted in abolishing the LC behavior. This small perturbation suggests that a polarized aromatic ring such as in entries 2 and 3 is necessary for LC formation in this class of mesogen.

Modifications of the N-terminus of the β-peptide were subsequently investigated. In this series of compounds the N-terminus was acylated and the hydrocarbon chain incrementally elongated. Acetylation resulted in a reduction of the minimum liquid crystal concentration to 2.5%, R=methanoyl, X═OH, (entry 6). An additional change of the C-terminus from a C-terminal amide to a C-terminal acid, did not change the minimum LC concentration (entry 7). This lack of change suggests the C-terminus is less sensitive to modifications. Further elongation of the acyl chain from ethanoyl to hexanoyl resulted in reducing the minimum concentration necessary to form an LC phase to 1 wt % (entries 8-12). However, acylation to form a benzoyl group abolished LC phase formation (entry 13) suggesting that not all substitution patterns at the N-terminus promote LC phases.

Figure 20:
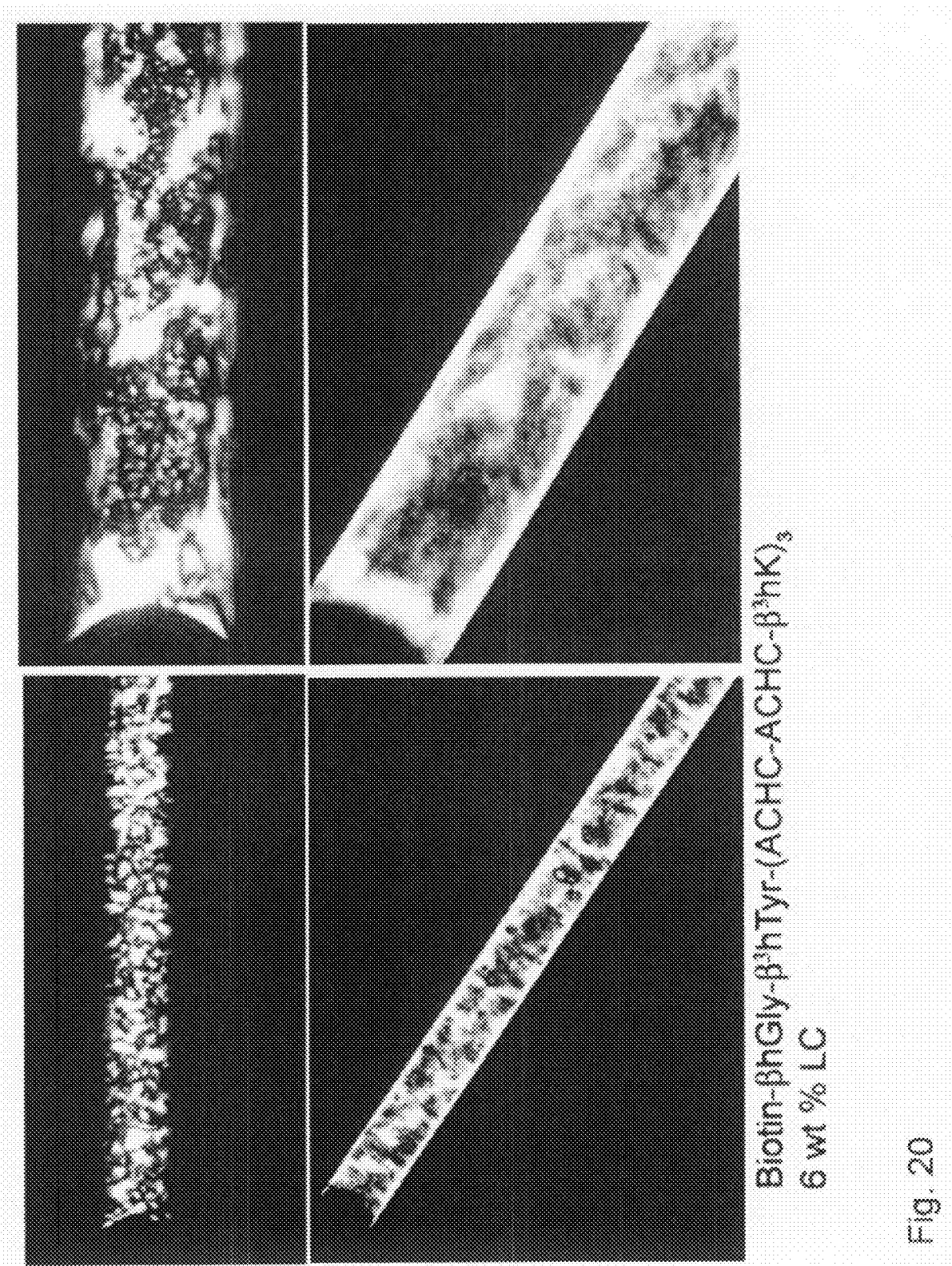
FIG. 20 provides optical micrographs of solutions of a β-peptide between crossed polarizing filters of the sequence biotin-βhGly-β$^3$hTyr-(ACHC-ACHC-β$^3$hLys)$_3$. Images were taken at two different orientations and magnifications.
Figure 21:
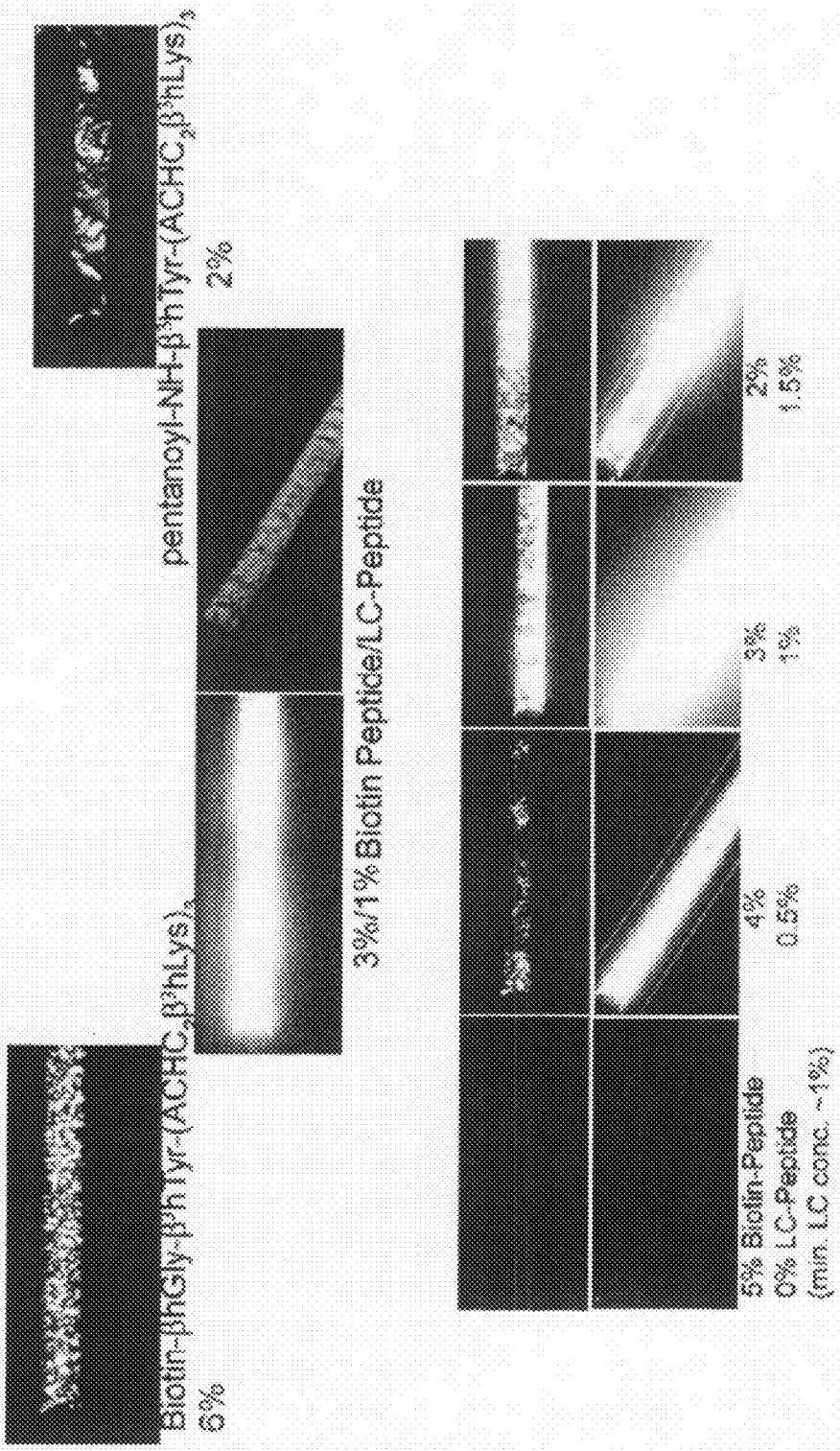
FIG. 21 provides optical micrographs illustrating the effect of mixing a liquid crystalline solution of pentanoyl-NH-β$^3$hTyr-(ACHC-ACHC-β$^3$hLys)$_3$ with biotin-βhGly-β$^3$hTyr-(ACHC-ACHC-β$^3$hLys)$_3$. An increase in birefringence suggests incorporation of the biotinylated compound into the liquid crystalline aggregate.

Finally, to highlight the modularity of the β-peptide mesogen, a small molecule epitope was also incorporated R=biotin-βhGly-, X=OH and was able to form an LC phase as low as 6 wt % (FIG. 19, entry 14). Liquid crystalline aggregates displaying biotin find use in biotechnology applications such as protein recognition on surfaces. The birefringent phase observed after formation of the liquid crystal is shown in FIG. 20. An alternative strategy for displaying biological epitopes within liquid crystalline aggregates is to mix in a fraction of the epitope displaying β-peptide with a previously discovered liquid crystal. An example of this behavior is shown in FIG. 21 where the two β-peptides are, R=biotin-βhGly-, X=OH, and R=pentanoyl, X=OH (FIG. 21). The increase in birefringence observed in mixing two β-peptides shows that there is a synergistic interaction between the two β-peptides indicating that the epitope has been incorporated into the liquid crystalline aggregate.

Example 5

Beta-peptides do Not Denature Proteins Under Physiological Conditions

The stability of proteins immobilized on a gold surface when exposed to a liquid crystal was investigated using streptavidin. Stability was assessed by monitoring the ability of immobilized streptavidin to bind a fluorescently labeled biotin molecule after the gold slide has been incubated with a liquid crystal. FIG. 22 shows that when the slide has been incubated with a pH 6.5 buffer, streptavidin is still able to bind biotin. However in the presence of sodium decyl sulfate SDeS, 32 wt %, the protein is denatured. Finally in the presence of a commercially available mesogen, disodium chromoglycate (DSCG), 16 wt %, or in the presence of the liquid crystal pentanoyl-$\beta^3$hTyr-(ACHC-ACHC-$\beta^3$hLys)$_3$ 1 wt %, streptavidin is still able to bind biotin. These results indicate that streptavidin is not denatured when exposed to the mesogenic β-peptide.

Example 6

Formation of Self-Assembled Nanofibers by Beta-peptides of the Invention

Figure 24:
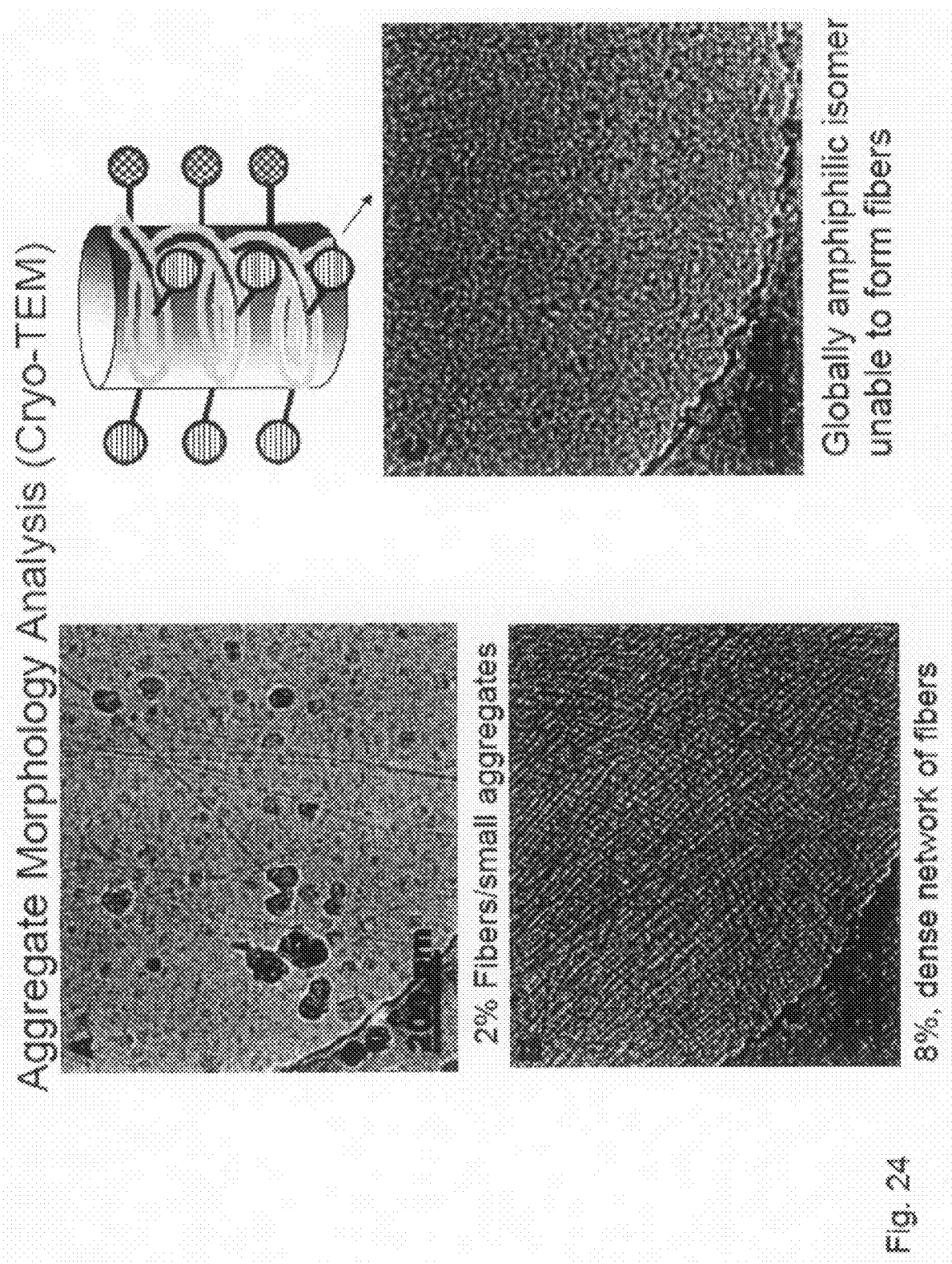
FIG. 24 provides cryo-TEM micrographs of A and iso-A top left) A, 2 wt %, bottom left) A, 8 wt %, right) iso-A, 8 wt %.

Based upon the inventors' data, it appears that LC phase formation requires β-peptide self-association, i.e., that the true mesogen in these systems is an aggregated form of the β-peptide. Onsager theory predicts that mesogens with a high aspect ratio will spontaneously form LC phases at a critical concentration through an entropy-driven process. This theory requires large aggregates (>500 monomers) if LC behavior is observed at concentrations as low as 2 wt %. Cryogenic-transmission electron microscopy (cryo-TEM) was undertaken in an effort to obtain further evidence for formation of high aspect ratio assemblies in lyotropic LC phases formed by β-peptides. At 2 wt % A, below the concentration required for LC phase formation, cryo-TEM revealed micron-long fibers intermixed with smaller globular aggregates (FIG. 23A). At 8 wt % A, which forms a lyotropic LC phase, a densely packed network of fibers was observed (FIG. 23B). Nanoscale assemblies of this type could correspond to the high aspect ratio mesogens predicted by Onsager theory which suggests that nanofibers generated by β-peptide self-assembly serve as the mesogenic species for LC phase formation. Only globular aggregates were observed in aqueous solutions of iso-A over the concentration range studied, consistent with the inability of this β-peptide to support lyotropic LC phase formation (FIG. 24 right; panels A and B from FIG. 23 are reproduced in FIG. 24 for comparative purposes). Nanofibers have also been observed for $\beta^3$-hTyr -(ACHC-$\beta^3$-hPhe-$\beta^3$-hLys)4 scram1 from 2.5-5 wt %, (FIG. 25) consistent with nanofibers being the active mesogen in LC phase formation.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A lyotropic liquid crystal comprising a β-peptide.
2. The lyotropic liquid crystal according to claim 1 further comprising an aqueous solvent wherein the β-peptide forms a helix in the aqueous solvent.
3. A lyotropic liquid crystal comprising a β-peptide and an aqueous solvent, wherein β-peptide forms a helix in the aqueous solvent, and wherein the β-peptide is globally amphiphilic.
4. A lyotropic liquid crystal comprising a β-peptide and an aqueous solvent, wherein the β-peptide forms a helix in the aqueous solvent, and wherein the β-peptide is globally non-amphiphilic.
5. A method of providing a β-peptide-based lyotropic liquid crystal, comprising the step of combining β-peptides capable of self-assembly under conditions to allow the self-assembly to occur whereby a β-peptide-based lyotropic liquid crystal is provided.
6. The method according to claim 5 wherein the β-peptide-based lyotropic liquid crystal comprises a β-peptide selected from the group consisting of:
 a β-peptide forming a globally amphiphilic helix;
 R-(ACHC-ACHC-$\beta^3$-hLys)$_n$ wherein n is 2-4 and R is $\beta^3$-hTyr or $\beta^3$-h-para-Cl-Phe;
 $\beta^3$-hTyr-(ACHC-AVHC-$\beta^3$hLys)$_2$ or $\beta^3$-hTyr-(ACHC-ACHC-$\beta^3$-hLys)$_3$;
 R-(ACHC-ACHC-$\beta^3$-hLys)$_3$ wherein R is $\beta^3$-hTyr or $\beta^3$-h-para-Cl-Phe and $\beta^3$-hLys at position 10 is substituted by $\beta^3$-hGlu;
 a β-peptide forming a globally non-amphiphilic helix;
 $\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-$\beta^3$-hLys-NH$_2$;
 $\beta^3$-hTyr-$\beta^3$-hLys-$\beta^3$-hPhe-ACHC-$\beta^3$-hPhe-X-ACHC-ACHC-$\beta^3$-hPhe-$\beta^3$-hLys-NH$_2$ or $\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-X-NH$_2$, wherein X is a hydrophilic amino acid;
 $\beta^3$-hTyr-$\beta^3$-hLys-$\beta^3$-hPhe-ACHC-$\beta^3$-hPhe-$\beta^3$-hLys-NH$_2$ or $\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-X-NH$_2$, wherein X is $\beta^3$-hGlu or $\beta^3$-hGln;

$\beta^3$-hTyr-$\beta^3$-hPhe-ACHC-$\beta^3$-hLys-$\beta^3$-hLys-$\beta^3$-hPhe-ACHC-$\beta^3$-hPhe-$\beta^3$-hLys-ACHC-ACHC$\beta^3$-hPhe-$\beta^3$-hLys-NH$_2$;

$\beta^3$-hTyr-$\beta^3$-hLys-$\beta^3$-hPhe-ACHC-$\beta^3$-hPhe-$\beta^3$-hLys-$\beta^3$-hPhe-ACHC-$\beta^3$-hPhe-$\beta^3$-hLys-ACHC-$\beta^3$-hLys-ACHC-NH$_2$;

CH$_3$(CH$_2$)$_n$CONH-$\beta^3$-hTyr-(ACHC-ACHC-$\beta^3$-hLys)$_3$ wherein n is 0-5; and biotin-$\beta^3$-hGly-$\beta^3$-hTyr-(ACHC-ACHC-$\beta^3$-hLys)$_3$.

7. A liquid crystal device for detecting an analyte in a sample, comprising: (a) a sample chamber; and (b) a $\beta$-peptide-based lyotropic liquid crystal positioned within the sample chamber, wherein the $\beta$-peptide-based lyotropic liquid crystal comprises a $\beta$-peptide selected from the group consisting of:

a $\beta$-peptide forming a globally amphiphilic helix;

R-(ACHC-ACHC-$\beta^3$-hLys)$_n$ wherein n is 2-4 and R is $\beta^3$-hTyr or $\beta^3$-h-para-Cl-Phe;

$\beta^3$-hTyr-(ACHC-ACHC-$\beta^3$-hLys)$_2$ or $\beta^3$-hTyr-(ACHC-ACHC-$\beta^3$-hLys)$_3$;

R-(ACHC-ACHC-$\beta^3$-hLys)$_3$ wherein R is $\beta^3$-hTyr or $\beta^3$-h-para-Cl-Phe and $\beta^3$-hLys at position 10 is substituted by $\beta^3$-hGlu;

a $\beta$-peptide forming a globally non-amphiphilic helix;

$\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-$\beta^3$-hLys-NH$_2$;

$\beta^3$-hTyr-$\beta^3$-hLys-$\beta^3$-hPhe-ACHC-$\beta^3$-hPhe-X-ACHC-ACHC-$\beta^3$-hPhe-$\beta^3$-hLys-NH$_2$ or $\beta^3$-hTyr-$\beta^3$-hLys-$\beta^3$-hPhe-ACHC-$\beta^3$-hPhe-$\beta$-hLys-ACHC-ACHC-$\beta^3$-hPhe-X-NH$_2$, wherein X is a hydrophilic amino acid;

$\beta^3$-hTyr-$\beta^3$-hLys-$\beta^3$-hPhe-ACHC-$\beta^3$-hPhe-X-ACHC-ACHC-$\beta^3$-hPhe-NH$_2$ or $\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-X—NH$_2$, wherein X is $\beta^3$-hGlu or $\beta^3$-hGln;

$\beta^3$-hTyr-$\beta^3$-hPhe-ACHC-$\beta^3$-hLys-$\beta^3$-hLys-$\beta^3$-hPhe-ACHC-$\beta^3$-hPhe-$\beta^3$-hLys-ACHC-ACHC-$\beta^3$-hPhe-$\beta^3$hLys-NH$_2$;

$\beta^3$-hTyr-$\beta^3$-hLys-$\beta^3$-hPhe-ACHC-$\beta^3$-hPhe-$\beta^3$-hLys-$\beta^3$-hPhe-ACHC-$\beta^3$-hPhe-$\beta^3$-hLys-ACHC-$\beta^3$-hLys-ACHC-NH$_2$;

CH$_3$(CH$_2$)$_n$CONH-$\beta^3$-hTyr-(ACHC-ACHC-$\beta^3$-hLys)$_3$ wherein n is 0-5; and biotin-$\beta^3$-hGly-$\beta^3$-hTyr-(ACHC-ACHC-$\beta^3$-hLys)$_3$.

8. A method of providing a network of self-assembled nanofibers, comprising the step of combining $\beta$-peptides capable of self-assembly under conditions to allow the self-assembly to occur whereby a network of self-assembled nanofibers is provided.

9. The method of claim 8 wherein at least one of the ($\beta$-peptides capable of self-assembly is a $\beta$-peptide selected from the group consisting of:

a $\beta$-peptide forming a globally amphiphilic helix;

R-(ACHC-ACHC-$\beta^3$-hLys)$_n$ wherein n is 2-4 and R is $\beta^3$-hTyr or $\beta^3$-h-para-Cl-Phe;

$\beta^3$-hTyr-(ACHC-ACHC-$\beta^3$-hLys)$_2$ or $\beta^3$-hTyr-(ACHC-ACHC-$\beta^3$-hLys)$_3$;

R-(ACHC-ACHC-$\beta^3$-hLys)$_3$ wherein R is $\beta^3$-hTyr or $\beta^3$-h-para-Cl-Phe and $\beta^3$-hLys at position 10 is substituted by $\beta^3$-hGlu;

a $\beta$-peptide forming a globally non-amphiphilic helix;

$\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-$\beta^3$-hLys-NH$_2$;

$\beta^3$-hTyr-$\beta^3$-hLys-$\beta^3$-hPhe-ACHC-$\beta^3$-hPhe-X-ACHC-ACHC-$\beta^3$-hPhe-$\beta^3$-hLys-NH$_2$ or $\beta^3$-hTyr-$\beta^3$-hLys-$\beta^3$-hPhe-ACHC-$\beta^3$-hPhe-$\beta$-hLys-ACHC-ACHC-$\beta^3$-hPhe-X—NH$_2$, wherein X is a hydrophilic amino acid;

$\beta^3$-hTyr-$\beta^3$-hLys-$\beta^3$-hPhe-ACHC-$\beta^3$-hPhe-X-ACHC-ACHC-$\beta^3$-hPhe-$\beta^3$-hLys-NH$_2$ or $\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-X-NH$_2$, wherein X is $\beta^3$-hGlu or $\beta^3$-hGln;

$\beta^3$-hTyr-$\beta^3$-hPhe-ACHC-$\beta^3$-hLys-$\beta^3$-hLys-$\beta^3$-hPhe-ACHC-$\beta^3$-hPhe-$\beta^3$-hLys-ACHC-ACHC-$\beta^3$-hPhe-$\beta^3$-hLys-NH$_2$;

$\beta^3$-hTyr-$\beta^3$-hLys-$\beta^3$-hPhe-ACHC-$\beta^3$-hPhe-$\beta^3$-hLys-$\beta^3$-hPhe-ACHC-$\beta^3$-hPhe-$\beta^3$-hLys-ACHC-$\beta^3$-hLys-ACHC-NH$_2$;

CH$_3$(CH$_2$)$_n$CONH-$\beta^3$-hTyr-(ACHC-ACHC-$\beta^3$-hLys)$_3$ wherein n is 0-5; and biotin-$\beta^3$-hGly-$\beta^3$-hTyr-(ACHC-ACHC-$\beta^3$-hLys)$_3$.

10. A lyotropic liquid crystal comprising a $\beta$-peptide, wherein the $\beta$-peptide is selected from the group consisting of:

R-(ACHC-ACHC-$\beta^3$-hLys)$_n$ wherein n is 2-4 and R is $\beta^3$-hTyr or $\beta^3$-h-para-Cl-Phe;

$\beta^3$-hTyr-(ACHC-ACHC-$\beta^3$-hLys)$_2$ or $\beta^3$-hTyr-(ACHC-ACHC-$\beta^3$-hLys)$_3$;

R-(ACHC-ACHC-$\beta^3$-hLys)$_3$ wherein R is $\beta^3$-hTyr or $\beta^3$-h-para-Cl-Phe and $\beta^3$-hLys at position 10 is substituted by $\beta^3$-hGlu;

$\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-$\beta^3$-hLys-NH$_2$;

$\beta^3$-hTyr-$\beta^3$-hLys-$\beta^3$-hPhe-ACHC-$\beta^3$-hPhe-X-ACHC-ACHC-$\beta^3$-hPhe-$\beta^3$-hLys-NH$_2$ or $\beta^3$- hTyr-$\beta^3$-hLys-$\beta^3$-hPhe-ACHC-$\beta^3$-hPhe-$\beta^3$-hLys-ACHC-ACHC-$\beta^3$-hPhe-X-NH$_2$, wherein X is a hydrophilic amino acid;

$\beta^3$-hTyr-$\beta^3$-hLys-$\beta^3$-hPhe-ACHC-$\beta^3$-hPhe-X-ACHC-ACHC-$\beta^3$-hPhe-$\beta^3$-hLys-NH$_2$ or $\beta^3$- hTyr-$\beta^3$-hLys-$\beta^3$-hPhe-ACHC-$\beta^3$-hPhe-13$^3$-hLys-ACHC-ACHC-$\beta^3$-hPhe-X-NH$_2$, wherein X is $\beta^3$-hGlu or $\beta^3$-hGln;

$\beta^3$-hTyr-$\beta^3$-hPhe-ACHC-$\beta^3$-hLys-$\beta^3$-hLys-$\beta^3$-hPhe-ACHC-$\beta^3$-hPhe-$\beta^3$-hLys-ACHC- ACHC-$\beta^3$-hPhe-$\beta^3$-hLys-NH$_2$;

$\beta^3$-hTyr-$\beta^3$-hLys-$\beta^3$-hPhe-ACHC-$\beta^3$-hPhe-$\beta^3$-hLys-$\beta^3$-hPhe-ACHC-$\beta^3$-hPhe-$\beta^3$-hLys- ACHC-$\beta^3$-hLys-ACHC-NH$_2$;

CH$_3$(CH$_2$)$_n$CONH-$\beta^3$-hTyr-(ACHC-ACHC-$\beta^3$-hLys)$_3$ wherein n is 0-5; and biotin-$\beta^3$-hGly-$\beta^3$-hTyr-(ACHC-ACHC-$\beta^3$-hLys)$_3$.

11. The lyotropic liquid crystal according to claim 10 wherein the $\beta$-peptide has the structure: R-(ACHC-ACHC-$\beta^3$-hLys)$_n$ wherein n is 2-4 and R is $\beta^3$-hTyr or $\beta^3$-h-para-Cl-Phe.

12. The lyotropic liquid crystal according to claim 11 wherein the $\beta$-peptide is $\beta^3$-hTyr-(ACHC-ACHC-$\beta^3$-hLys)$_2$ or $\beta^3$-hTyr-(ACHC-ACHC-$\beta^3$-hLys)$_3$.

13. The lyotropic liquid crystal according to claim 10 wherein the $\beta$-peptide has the structure: R-(ACHC-ACHC-$\beta^3$-hLys)$_3$ wherein R is $\beta^3$-hTyr or $\beta^3$-h-para-Cl-Phe and $\beta^3$-hLys at position 10 is substituted by $\beta^3$-hGlu.

14. The lyotropic liquid crystal according to claim 10 wherein the $\beta$-peptide is $\beta^3$-hTyr-$\beta^3$-hLys-$\beta^3$-hPhe-ACHC-$\beta^3$-hPhe-$\beta^3$-hLys-ACHC-ACHC-$\beta^3$-hPhe-$\beta^3$-hLys-NH$_2$.

15. The lyotropic liquid crystal according to claim 10 wherein the $\beta$-peptide is $\beta^3$-hTyr-$\beta^3$-hLys-$\beta^3$-hPhe-ACHC-$\beta^3$-hPhe-X-ACHC-ACHC-$\beta^3$-hPhe-$\beta^3$-hLys-NH$_2$ or $\beta^3$-hTyr-$\beta^3$-hLys-$\beta^3$-hPhe-ACHC- $\beta^3$-hPhe-$\beta^3$-hLys-ACHC-ACHC-$\beta^3$-hPhe-X-NH$_2$, wherein X is a hydrophilic amino acid.

16. The lyotropic liquid crystal according to claim 15 wherein X is $\beta^3$-hGlu or $\beta^3$-hGln.

17. The lyotropic liquid crystal according to claim 10 wherein the β-peptide is $\beta^3$-hTyr-$\beta^3$-hPhe-ACHC-$\beta^3$-hLys-$\beta^3$-hLys-$\beta^3$-hPhe-ACHC-$\beta^3$-hPhe-$\beta^3$-hLys-ACHC-ACHC-$\beta^3$-hPhe-$\beta^3$-hLys-NH$_2$.

18. The lyotropic liquid crystal according to claim 10 wherein the β-peptide is $\beta^3$-hTyr-$\beta^3$-hLys-$\beta^3$-hPhe-ACHC-$\beta^3$-hPhe-$\beta^3$-hLys-$\beta^3$-hPhe-ACHC-$\beta^3$-hPhe-$\beta^3$-hLys-ACHC-$\beta^3$-hLys-ACHC-NH$_2$.

19. The lyotropic liquid crystal according to claim 10 wherein the β-peptide is CH$_3$(CH$_2$)$_n$CONH-$\beta^3$-hTyr-(ACHC-ACHC-$\beta^3$-hLys)$_3$ wherein n is 0-5.

20. The lyotropic liquid crystal according to claim 10 wherein the β-peptide is biotin-$\beta^3$-hGly-$\beta^3$-hTyr-(ACHC-ACHC-$\beta^3$-hLys)$_3$.

* * * * *